United States Patent [19]

Martuza et al.

[11] Patent Number: 5,585,096
[45] Date of Patent: Dec. 17, 1996

[54] REPLICATION-COMPETENT HERPES SIMPLEX VIRUS MEDIATES DESTRUCTION OF NEOPLASTIC CELLS

[75] Inventors: Robert L. Martuza, Chevy Chase; Samuel D. Rabkin; Toshihiro Mineta, both of Bethesda, all of Md.

[73] Assignee: Georgetown University, Washington, D.C.

[21] Appl. No.: 264,581

[22] Filed: Jun. 23, 1994

[51] Int. Cl.⁶ .......................... A01N 63/00; A61K 48/00; A61K 39/12; A61K 39/245

[52] U.S. Cl. .................. 424/93.2; 424/205.1; 424/229.1; 435/172.3; 435/235.1; 435/236; 435/320.1; 935/32

[58] Field of Search ........................... 424/205.1, 229.1, 424/93.2; 435/236, 235.1, 320.1, 172.3; 935/32

[56] References Cited

U.S. PATENT DOCUMENTS

| | | | |
|---|---|---|---|
| 4,322,404 | 3/1982 | Gauri et al. | 424/89 |
| 5,328,688 | 7/1994 | Roizman | 424/205.1 |

OTHER PUBLICATIONS

Markert et al (1993) Neurosurgery 32: 597–603.

Neurosurgery, vol. 26, No. 5, (1990) Lichtor et al., "Cytokine Gene Expression by Human Gliomas", pp. 788–793.

Journal of Cancer Research and Clinical Oncology, vol. 120 (supplement), (1994), Hart et al., "The Use of Tissue–Specific Promoters to Target Gene Therapy to Malignant Melanoma" p. R1.

British Journal of Cancer, vol. 63, (1991), Tuzi et al., "Expression of Growth Factor Receptors in Human Brain Tumors", pp. 227–233.

Proceedings of the National Academy of Science, USA, vol. 90, (1993), Plautz et al., "Immunotherapy of Malignancy by in vivo Gene Transfer into Tumors", pp. 4645–4649.

McLauchlan et al., "DNA Sequence Homology Between Two Co–Linear Loci–On The HSV Genome Which Have Different Transforming Abilities", *The EMBO Journal*, vol. 2: 1953–1961, (1983).

Swain et al., "Herpes Simplex Virus Specifics Two Subunits of Ribonucleotide Reductase Encoded By 3'–Coterminal Transcripts", *Journal of Virology*, vol. 57:802–808, (1986).

Dutia, "Ribonucleotide Reductase Induced By Herpes Simplex virus Has A Virus–Specified Constitutent", *J. Gen. Virol.*, vol. 64:513–521, (1983).

McLauchlan et al., "Organization Of The Herpes Simplex Virus Type 1 Transcription Unit Encoding Two Early Proteins With Molecular Weights of 140,00 And 40,000", *J. Gen. Virol.*, 64:997–1006, (1983).

McGeoch et al., "Comparative Sequence Analysis Of The Long Repeat Regions And Adjoining Parts Of The Long Unique Regions In The Genomes Of Herpes Simplex Viruses Types 1 And 2", *Journal of General Virology*, vol. 72:3057–3075, (1991).

Perry et al., "The DNA Sequence Of The Long Repeat Regions And Adjoining Parts Of The Long Unique Region In The Genome Of Herpes Simplex Virus Type 1", *J. Gen. Virol.*, vol. 69:2831–2846, (1988).

(List continued on next page.)

*Primary Examiner*—Bruce R. Campell
*Attorney, Agent, or Firm*—Foley & Lardner

[57] ABSTRACT

A method for killing malignant brain tumor cells in vivo entails providing replication competent herpes simplex virus vectors to tumor cells. A replication competent herpes simplex virus vector, with defective expression of the ɣ34.5 gene and the ribonucleotide reductase gene, specifically destroys tumor cells, is hypersensitive to anti-viral agents, and yet is not neurovirulent.

8 Claims, 5 Drawing Sheets

OTHER PUBLICATIONS

Jacobson et al., "A Herpes Simplex Virus Ribonucleotide Reductase Deletion Mutant Is Defective For Productive Acute And Reactivatable Latent Infections Of Mice And For Replication In Mouse Cells", *Virology*, vol. 173:276–283, (1989).

Sze et al., "The Herpes Simplex virus Type 1 ICP6 Gene Is Regulated By A 'Leaky' Early Promoter", *Virus Research*, vol. 26:141–152, (1992).

Goldstein et al., "Herpes Simplex Virus Type 1–Induced Ribonucleotide Reductase Acitvity Is Dispensable For Virus Growth And DNA Synthesis: Isolation And Characterization Of An ICP6 IacZ Insertion Mutant", *Journal of Virology*, vol. 62:196–205, (1988).

Nikas et al., "Structural Features Of Ribonucleotide Reductase", *Proteins: Structure, Function, and Genetics*, vol. 1:376–384, (1986).

Huszar et al., "Partial Purification And Characterization Of The Ribonucleotide Reductase Induced By Herpes Simplex Virus Infection Of Mammalian Cells", *Journal of Virology*, 37:580–588, (1981).

Cameron et al., "Ribonucleotide Reductase Encoded By Herpes Simplex Virus Is Determinant Of The Pathogenicity Of The Virus In Mice And A Valid Antiviral Target", *J. gen. Virol.*, vol. 69:2607–2612, (1988).

McGeoch et al., "Sequence Determination And Genetic content Of The Short Unique Region In The Genome Of Herpes Simplex Virus Type 1", J. Mol. Biol., vol. 181:1–13, (1985).

McGeoch et al., "Complete DNA Sequence Of The Short Repeat In The Genome Of Herpes Simplex Virus Type 1", *Nucleic Acids Research*, vol. 14:1727–1745, (1986).

McGeoch et al., "The Complete DNA Sequence Of The Long Unique Region In The Genome Of Herpes Simplex Virus Type 1", *J. gen. Virol.*, vol. 69:1531–1574, (1988).

Mckie et al., "Characterization Of The Herpes Simplex Virus Type 1 Strain 17+Neurovirulence Gene RL1 And Its Expression In A Bacterial System", *Journal Of General Virology*, vol. 75:733–741, (1994).

Chou et al., "The Herpes Simplex Virus 1 Gene For ICP34.5, Which Maps In Inverted Repeats, Is Conserved In Several Limited–Passage Isolates But Not In Strain 17syn+ ", *Journal Of Virology*, vol. 64:1014–1020, (1990).

Roizman et al., "Genetic Engineering Of Novel Genomes Of Large DNA Viruses", *Science*, vol. 229:1208–1214, (1985).

Goodman et al., "Identification, Transfer, And Characterization Of Cloned Herpes Simplex Virus Invasiveness Regions", *Journal Of Virology*, vol. 63:1153–1161, (1989).

Chou et al., "The Terminal $\alpha$ Sequence Of The Herpes Simplex Virus Genome Contains The Promoter Of A Gene Located In The Repeat Sequences Of The L Component", *Journal Of Virology*, vol. 57:629–637, (1986).

Chou et al., "Mapping Of Herpes Simplex Virus–1 Neurovirulence To $y_1 34.5$, A Gene Nonessential For Growth In Culture", *Science*, vol. 250:1262–1266, (1990).

Bolovan et al., "ICP34.5 Mutants Of Herpes Simplex Virus Type 1 Strain 17syn + Are Attenuated For Neurovirulence In Mice And For Replication In Confluent Primary Mouse Embryo Cell Cultures", *Journal of Virology*, vol. 68:48–55, (1994).

Chou et al., "The $y_1 34.5$ Gene Of Herpes Simplex Virus 1 Precludes Neuroblastoma Cells From Triggering Total Shutoff Of Protein Synthesis Characteristic Of Programmed Cell Death In Neuronal Cells", *Proc. Natl. Acad. Sci. USA*, vol. 89:3266–3270, (1992).

REPLICATION-COMPETENT HERPES SIMPLEX VIRUS MEDIATES DESTRUCTION OF NEOPLASTIC CELLS

BACKGROUND OF THE INVENTION

The present invention relates to the use of an altered herpes simplex virus that is capable of killing tumor cells. More specifically, the present invention relates to a mutated, replication-competent Herpes Simplex Virus-1 (HSV-1) which contains mutations in two genes, is hypersensitive to antiviral agents such as acyclovir, is not neurovirulent and does not replicate in non-dividing cells, yet can kill nervous system tumor cells.

Malignant tumors of the nervous system usually are fatal, despite many recent advances in neurosurgical techniques, chemotherapy and radiotherapy. In particular, there is no standard therapeutic modality that has substantially changed the prognosis for patients diagnosed with malignant brain tumors. For example, high mortality rates persist in malignant medulloblastomas, malignant meningiomas and neurofibrosarcomas, as well as in malignant gliomas.

Gliomas are the most common primary tumors arising in the human brain. The most malignant glioma, the glioblastoma, represents 29% of all primary brain tumors, some 5,000 new cases per year in the United States alone. Glioblastomas are almost always fatal, with a median survival of less than a year and a 5-year survival of 5.5% or less. Mahaley et al., *J. Neurosurg.* 71: 826 (1989); Shapiro, et al., *J. Neurosurg.* 71: 1 (1989); Kim et al., *J. Neurosurg.* 74: 27 (1991). After glioblastomas are treated with radiotherapy, recurrent disease usually occurs locally; systemic metastases are rare. Hochberg et al., *Neurology* 30: 907 (1980). Neurologic dysfunction and death in an individual with glioblastoma is due to the local growth of the tumor.

In the past, viruses have been tested for their ability to treat various types of tumors in animals or humans. The proposed therapeutic mechanisms of viral cancer therapy in the prior art includes: (i) producing new antigens on the tumor cell surface to induce immunologic rejection, a phenomenon called "xenogenization", and (ii) direct cell killing by the virus, called oncolysis. Austin et al., *Adv. Cancer Res.* 30: 301 (1979); Kobayashi et al., *Adv. Cancer Res.* 30: 279 (1979); Moore, *Progr. Exp. Tumor Res.* 1: 411 (1960). Treatments for tumors in both animals and in humans have been based on wild-type virus, passage attenuated virus, or infected cell preparations. Kobayashi, *Adv. Cancer Res.* 30: 279 (1979); Cassel et al., *Cancer* 52: 856 (1983); Moore, *Prog. Exp. Tumor Res.* 1: 411 (1960).

Several animal models and animal tumors have been used to study oncolysis with wild-type viruses. Moore, *Ann. Rev. Microbiol.* 8: 393 (1954); Moore, *Progr. Exp. Tumor Res.* 1: 411 (1960). At least nine viruses have been shown to be capable of inducing some degree of tumor regression in a variety of tumors in mice, rats, rabbits, and guinea pigs. A major drawback seen in these early animal studies, however, was systemic infection by the virus.

To avoid systemic infection, the genetic engineering of viruses for use as antineoplastic agents has focused on generating altered viruses that are not capable of replication in non-dividing cells. Viruses capable of replication in dividing cells preferentially infect rapidly dividing tumor cells because they are incapable of replicating in non-dividing normal cells.

The use of replication-incompetent or defective viruses, which require helper virus to be able to integrate and/or replicate in a host cell, was hoped to prevent damage to non-tumor cells. The replication-defective herpes simplex virus vector system consists of an amplicon plasmid which, in herpes simplex virus infected cells, is replicated and packaged into viral particles. Defective herpes simplex virus vectors require helper virus to generate a herpes simplex virus vector.

The use of replication-defective retroviruses for treating nervous system tumors requires producer cells and has been shown to be limited because each replication-defective retrovirus particle can enter only a single cell and cannot productively infect others thereafter. Because these replication-defective retroviruses cannot spread to other tumor cells, they would be unable to completely penetrate a deep, multilayered tumor in vivo. Markert et al., *Neurosurg.* 77: 590 (1992).

Clinical trials employing retroviral vector therapy treatment of cancer have been approved in the United States. Culver, *Clin. Chem* 40: 510 (1994). Retroviral vector-containing cells have been implanted into brain tumors growing in human patients. Oldfield et al., *Hum. Gene Ther.* 4: 39 (1993). These retroviral vectors carried the HSV-1 thymidine kinase (HS-tk) gene into the surrounding brain tumor cells, which conferred sensitivity of the tumor cells to the anti-herpes drug ganciclovir. Of eight patients with recurrent glioblastoma multiforme or metastatic tumors treated by stereotactic implantation of murine fibroblast cells producing retroviral vectors, five patients demonstrated some evidence of anti-tumor efficacy but none were cured. Culver, supra (1994). Some of the limitations of current retroviral based therapy as described by Oldfield are (1) the low titer of virus produced, (2) virus spread limited to the region surrounding the producer cell implant, (3) possible immune response to the producer cell line, (4) possible insertional mutagenesis and transformation of retroviral infected cells, (5) single treatment regimen of pro-drug, ganciclovir, because the "suicide" product kills retrovirally infected cells and producer cells and (6) the bystander effect limited to cells in direct contact with retrovirally transformed cells. Bi, W. L. et al., *Human Gene Therapy* 4: 725 (1993).

In the early 1990's, the use of genetically engineered replication-competent HSV-1 viral vectors was first explored in the context of antitumor therapy. Martuza et al., *Science* 252: 854 (1991). A replication-competent virus has the advantage of being able to enter one tumor cell, make multiple copies, lyse the cell and spread to additional tumor cells. A thymidine kinase-deficient (TK$^-$) mutant, dlsptk, was able to destroy human malignant glioma cells in an animal brain tumor model. Martuza, supra (1991). Unfortunately, the dlsptk mutants were only moderately attenuated for neurovirulence and produce encephalitis at the doses required to kill the tumor cells adequately. Markert et al., *Neurosurgery* 32: 597 (1993). Residual neurovirulence, as evidenced by a 50% lethality of intracranially-administered, replication-deficient herpes simplex virus viral vectors at $10^6$ plaque forming units (pfu) limits the use of such vectors for tumor therapy. Furthermore, known TK$^-$ HSV-1 mutants are insensitive to acyclovir and ganciclovir, the most commonly used and efficacious anti-herpetic agents.

Therefore, it remains of utmost importance to develop a safe and effective viral vector for killing tumor cells. Even though various attempts have been made to engineer a viral vector able to kill human tumor cells in vivo, no viral vector has provided attenuated neurovirulence at the dose required to kill tumor cells while exhibiting hypersensitivity to antiviral agents and an inability to revert to wild-type virus. Currently, no viral vector has been demonstrated to meet these criteria.

SUMMARY OF THE INVENTION

It is therefore an object of this invention to provide a replication-competent viral vector, suitable for use in humans, that is capable of killing human tumor cells in vivo, that exhibits hypersensitivity to anti-viral agents and an inability to revert to wild-type virus, and that is not neurovirulent at a dose required to kill tumor cells.

It is another object of the present invention to provide for the production of a replication-competent, herpes simplex virus-derived vector that is effective and safe for use in the treatment of malignant brain tumors in humans.

It is a further object of the invention to provide a safe, mutated HSV-1 vector, for use in the context of a vaccine or tumor therapy, which vector is incapable of reverting to wild-type form through a spontaneous single mutation.

Still another object of the present invention is to provide a mutant HSV-1 vector that can selectively replicate in and kill a tumor cell of non-nervous tissue origin.

An additional object of the present invention is the production of a replication-competent viral vector, derived from herpes simplex virus, which can be employed in a genetic therapy against tumors by expressing foreign genes to target an immune response that kills the tumor cells.

Yet another object of the present invention is the production of a mutant herpes simplex virus vector containing a tumor cell-specific promoter so that the vector can be targeted to specific tumor cells.

It is also an object of the present invention to provide for production of a replication competent viral vector that is effective and safe for use as a vaccine to protect against infection by herpes simplex virus.

In satisfying these and other objects, there has been provided, in accordance with one aspect of the present invention, a replication-competent herpes simplex virus that is incapable of expressing both (i) a functional $\gamma_134.5$ gene product and (ii) a ribonucleotide reductase. In a preferred embodiment, the vector contains alterations in both genes.

In accordance with another aspect of the present invention, a method has been provided for killing tumor cells in a subject, comprising the step of administering to the subject a pharmaceutical composition comprising (A) a herpes simplex virus vector that is altered in (i) the $\gamma_134.5$ gene, and (ii) the ribonucleotide reductase gene; and (B) a pharmaceutically acceptable vehicle for the vector, such that the tumor cells are altered in situ by the vector and the tumor cells are killed. The tumor cells can be of a nervous-system type selected from the group consisting of astrocytoma, oligodendroglioma, meningioma, neurofibroma, glioblastoma, ependymoma, Schwannoma, neurofibrosarcoma, and medulloblastoma. Other kinds of tumor cells which can be killed, pursuant to the present invention, include those selected from the group consisting of melanoma cells, pancreatic cancer cells, prostate carcinoma cells, breast cancer cells, lung cancer cells, colon cancer cells, lymphoma cells, hepatoma cells and mesothelioma and epidermoid carcinoma cells.

In accordance with still another aspect of the present invention, a method is provided for killing tumor cells in a subject, comprising the steps of administering to the subject a herpes simplex virus vector, wherein the vector comprises a tumor cell-specific promoter wherein the promoter controls expression of at least one viral protein necessary for viral replication and wherein the promoter is induced selectively or at a higher level in tumor cells than in normal cells. This method can entail the use of a promoter that is selectively capable of expression in nervous-system tumor cells, for example, glioblastoma cells, medulloblastoma cells, meningioma cells, neurofibrosarcoma cells, astrocytoma cells, oligodendroglioma cells, neurofibroma cells, ependymoma cells and Schwannoma cells.

A method also in provided for preparing a replication-competent vector of a herpes simplex virus, comprising the steps of (A) isolating a viral genome of the herpes simplex virus; and (B) permanently altering the genome so that the virus is (1) sensitive to antiviral agents, (2) kills tumor cells and (3) expresses decreased generalized neurovirulence. For example, the the herpes simplex virus of the vector can be HSV-1 or HSV-2.

The present invention further provides for a method of protecting a subject against herpes simplex virus infection, comprising the step of administering to the subject a pharmaceutical composition that is comprised of (A) a herpes simplex virus vector wherein the genome of the virus is altered in (i) the $\gamma_134.5$ gene, and (ii) the ribonucleotide reductase gene; and (B) a pharmaceutically acceptable vehicle for the vector.

According to still another aspect of the present invention, there has been provided a method of eliciting an immune response to a tumor cell, comprising the step of administering to the subject a pharmaceutical composition comprising (A) a herpes simplex virus, wherein the genome of the virus (i) contains an expressible non-herpes simplex virus nucleotide sequence encoding a desired protein capable of eliciting an immune response in the subject, and (ii) is altered in the $\gamma_134.5$ gene, and the ribonucleotide reductase gene; and (B) a pharmaceutically acceptable vehicle for the virus. In a preferred embodiment, the method further comprises the step of co-administration with neurosurgery, chemotherapy or radiotherapy.

A mutant viral vector of the present invention is sensitive to temperatures greater than the basal temperature of the host, which provides an additional safety feature by further compromising viral replication in the presence of encephalitis and fever.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention can be understood more fully by reference to the following drawings, where.

DETAILED DESCRIPTION OF THE PREFERRED EMBODIMENTS

Figure 1:
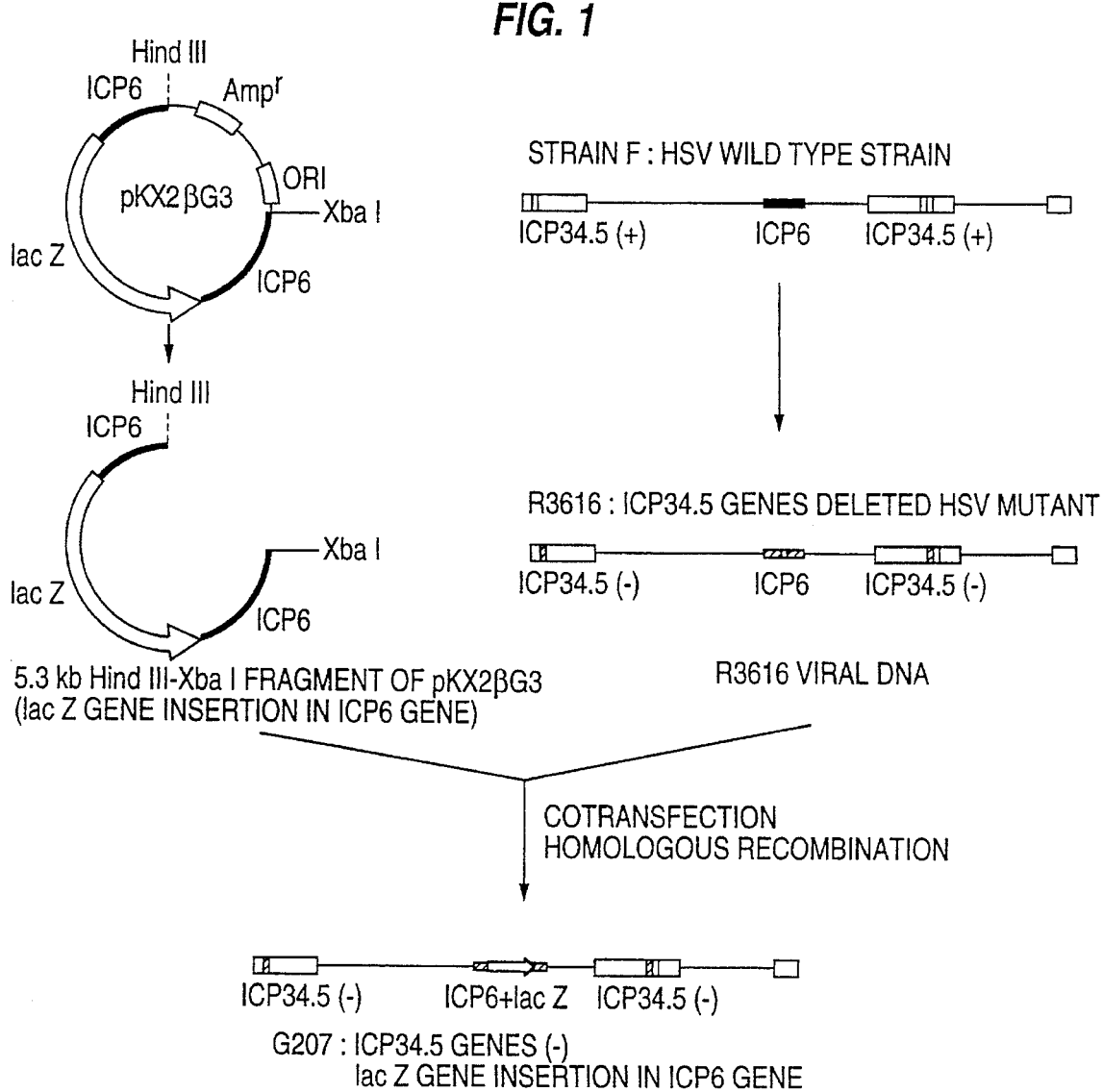
FIG. 1 is a schematic illustration of the construction of a mutant herpes simplex virus containing a 1 kB deletion in both copies of the $\gamma_134.5$ gene and an insertion in the ICP6 gene.

The present invention exploits the ability of mutant, replication-competent HSV-1 to enter a tumor cell in situ, make multiple copies, lyse the tumor cell and spread to additional tumor cells with relatively minor effects on the surrounding normal cells. The mutant herpes simplex virus of the present invention has each of the following characteristics: (1) efficacy in killing human brain tumor cells, (2) marked attenuation of generalized neurovirulence to protect the normal brain, (3) multiple deletions so that a single mutation cannot cause reversion to the wild-type viral phenotype, and (4) hypersensitivity to ganciclovir so that undesired spread of the virus can be prevented. The mutant virus of the present invention is capable of replicating in neoplastic cells but spares surrounding non-neoplastic tissue.

Viruses of the instant invention are engineered to contain alterations in the expression of at least two specific HSV-1 genes: (1) the $\gamma_1 34.5$ gene and (2) the ribonucleotide reductase gene. Alterations in this regard include any that disrupt the expression of the product of both of the $\gamma_1 34.5$ gene and the ribonucleotide reductase gene. The presence of such multiple mutations further reduces the possibility of reversion to wild-type pathogenicity. The present invention provides methods for sequentially constructing and testing viruses for the ability to effectively kill brain tumor cells without harming surrounding normal brain. Additionally, mutations can be inserted into these vectors to increase their sensitivity to systemically administered drugs.

Herpes Simplex Virus Vectors with Single Alterations in the Ribonucleotide Reductase or $\gamma_1 34.5$ Gene Initial work on the use of attenuated herpes simplex virus vectors for use in anti-tumor therapy employed HSV-1 mutated in one gene allowing the vector to replicate in dividing cells, but not in non-dividing cells. Two such single gene-mutant herpes simplex virus vectors are (1) hrR3, deficient in ribonucleotide reductase, containing an *Escherichia coli* lacZ gene insertion in the ICP6 gene that encodes the large subunit of RR, [Mineta, T. et al., *Gene Therapy* 1:S78 (1994) and Mineta et al., *J. Neurosurg.* 80: 381 (1994)]; and (2) R3616, which contains mutations in both copies of the $\gamma_1$–34.5 gene. Markert et al., *Neurosurgery* 32: 597 (1993).

Mutants of ribonucleotide reductase have been constructed by a number of methods. The hrR3 mutant contains an *Escherichia coli* lacZ gene insertion in the ICP6 gene, which encodes the large subunit of ribonucleotide reductase. Other ribonucleotide reductase herpes simplex virus mutants are suitable for constructing the mutant viral vector of the invention. Goldstein and Weller, supra; Goldstein and Weller, supra; Preston et al., *Virol.* 167: 458 (1988).

Ribonucleotide reductase (RR) is a key enzyme in the de novo synthesis of DNA precursors, catalyzing the reduction of ribonucleotides to deoxyribonucleotides. HSV-1 encodes its own RR (UL39 and UL40 genes), which is composed of two non-identical subunits. Duita, *J. Gen. Virol.* 64: 513 (1983). The large subunit (140k molecular weight), designated ICP6, is tightly associated with the small subunit (38k molecular weight). Herpes simplex virus RR is required for efficient viral growth in non-dividing cells but not in many dividing cells. Goldstein and Weller, *J. Virol.* 62: 196 (1988); Goldstein and Weller, *Virol.* 166: 41 (1988); Jacobson et al., *Virol.* 173: 276 (1989). Both RR subunits are present in HSV-2. It is noted that HSV-1 ICP6 is the same as HSV-2 ICP10. Nikas et al., *Proteins* 1: 376 (1986); McLaughlan and Clements *EMBO J.* 2: 1953 (1983); Swain and Halloway *J Virol.* 57: 802 (1986)] and mutations in the small subunit of RR also leads to loss of RR activity and neuropathogenicity [Cameron et al., *J. Gen. Virol.* 69: 2607 (1988)]. The presence of the lacZ gene in hrR3 allows identification of virally-infected tumor cells using β-galactosidase histochemistry.

The cytopathic effect of hrR3 (0.1 pfu/cell) on the U-87MG human glioblastoma cell line in vitro was significant; only 0.2% of U-87MG cells were alive 67 hours post-infection. For in vivo studies, ten animals harboring U-87MG tumors were randomly divided and treated intraneoplastically with either $5 \times 10^5$ plaque-forming units of hrR3 or with medium alone. The viral treatment group showed significant inhibition of tumor growth (p<0.01, one-sided Wilcoxon rank test).

An important difference between ribonucleotide reductase deficient (RR$^-$) and other herpes simplex virus mutants is hrR3's hypersensitivity to acyclovir and ganciclovir. Because TK$^-$ HSV-1 mutants known in the art are resistant to these anti-viral agents, such mutants could be difficult to eliminate in the event of systemic infection or encephalitis. Thus, in the event of viral encephalitis, hrR3 is responsive to antiviral therapy.

Also, herpes simplex virus RR- mutants are severely compromised in their ability to produce infections and synthesize viral DNA at 39.5° C. in vitro. Goldstein and Weller, *Virology* 166: 41 (1988). Therefore, these mutants are attenuated for neurovirulence and less likely to propagate in the event of a fever in the infected host. Such characteristics are essential to a therapeutic vector which must be of attenuated neurovirulence and amenable to antiviral therapy in the event of viral encephalitis.

Herpes simplex virus mutants deficient in only the $\gamma_1 34.5$ gene, such as R3616, are attenuated for neurovirulence, which reduces the possible damage to normal brain cells. Goodman et al., *J. Virol.* 63: 1153 (1989); Chou et al., *Science* 250: 1262 (1990). The decreased neurovirulence of R3616 is putatively associated with the cessation of neuronal protein synthesis, which is preempted in wild-type herpes simplex virus infection. Chou and Roizman, *Proc. Nat'l Acad. Sci. USA* 89: 3266 (1992). The $\gamma_1 34.5$ gene product can be detected by Western blot or ELISA analysis of infected cell proteins with antibodies or lack of replication in confluent primary cells. See Bolovan et al., *J. Virol.* 68: 48 (1994). The $\gamma_1 34.5$ gene is also present in HSV-2. McGeoch et al., *J. Gen. Virol.* 72: 3057 (1991). The $\gamma_1 34.5$ gene has been sequenced in four strains of HSV-1, namely F, 17, MGH-10 and CVG-2. Chou and Roizman, *J. Virol.* 64: 1014 (1990). The $\gamma_1 34.5$ gene mutant HSV-1 vectors retain a wild-type level of sensitivity to acyclovir. Markert et al., supra (1993).

Mutants of $\gamma_1 34.5$ have been constructed by various investigators using different techniques and in different strains such as mutant 1771 (McKie et al., *J. Gen. Virol.* 75: 733 (1994)] and 17termA [Bolovan et al., *J. Virol.* 68: 48 (1994)] in HSV-1 strain 17.

Construction of Herpes Simplex Virus Vectors

HSV-1 is a human neurotropic virus that is capable of infecting virtually all vertebrate cells. Natural infections follow either a lytic, replicative cycle or establish latency, usually in peripheral ganglia, where the DNA is maintained indefinitely in an episomal state.

Replication-competent recombinant herpes simplex virus vectors of the instant invention contain alterations in expression of two specific herpes simplex virus genes: (1) the $\gamma 34.5$ gene and (2) the ribonucleotide reductase gene. Such alterations render the product of both genes non-functional or reduce their expression such that the mutant herpes simplex virus vector has the properties of the instant invention. Ways to achieve such alterations include (a) any method to disrupt the expression of the product of both of these genes or (b) any method to render the expressed $\gamma 34.5$ gene product and ribonucleotide reductase nonfunctional.

Numerous methods known to disrupt the expression of a gene are known, including the alterations of these genes or their promoter sequences in the HSV-1 genome by insertions, deletions and/or base changes. Roizman and Jenkins, *Science* 229: 1208 (1985). The mutated herpes simplex virus vector of the instant invention is a replication competent herpes simplex virus whose genome is altered in the $\gamma 34.5$ gene and the ribonucleotide reductase gene. Alterations in the $\gamma 34.5$ gene and the ribonucleotide reductase gene include modifications in either the structural or regulatory sequences of these genes. Genetic alterations can be determined by standard methods such as Southern blot hybridization of restriction endonuclease digested viral DNA, sequencing of mutated regions of viral DNA, presence of reporter gene (for insertions), new restriction endonuclease site, enzymatic assay for ribonucleotide reductase activity [Huszar and Bacchetti, *J. Virol.* 37: 580 (1981)], Western blot or ELISA analysis of infected cell proteins with antibodies to RR or $\gamma 34.5$, and/or lack of replication in confluent primary cells for $\gamma 34.5$. See Bolovan et al., *J. Virol.* 68: 48 (1994)] or mouse cells for RR- [Jacobson et al., *Virology* 173: 276 (1989).

The following genetic manipulations of herpes simplex virus provide examples to illustrate the production of mutant herpes simplex virus vectors. The engineering of the herpes simplex virus vectors of the instant invention exploit two well-characterized genes, the $\gamma 34.5$ and ribonucleotide reductase genes, in a biologically well-characterized virus.

A herpes simplex virus vector that has been mutated in its $\gamma 34.5$ and ribonucleotide reductase genes can be isolated after mutagenesis or constructed via recombination between the viral genome and genetically-engineered sequences. The high rate of recombination in herpes simplex virus and the fact that transfected viral DNA is infectious renders genetic manipulation very straightforward. These genetically-altered, replication-competent viruses can be used in the safety and efficacy assays described below.

HSV-1 contains a double-stranded, linear DNA genome, 153 kilobases in length, which has been completely sequenced by McGeoch. McGeoch et al., *J. Gen. Virol.* 69: 1531 (1988). McGeoch et al., *Nucleic Acids Res* 14: 1727 (1986); McGeoch et al., *J. Mol. Biol.* 181: 1 (1985); Perry and McGeoch, *J. Gen. Virol.* 69: 2831 (1988). DNA replication and virion assembly occurs in the nucleus of infected cells. Late in infection, concatemeric viral DNA is cleaved into genome length molecules which are packaged into virions. In the CNS, herpes simplex virus spreads transneuronally followed by intraaxonal transport to the nucleus, either retrograde or anterograde, where replication occurs.

DNA constructs employing HSV-2 based on those illustrated herein using the HSV-1 genome are encompassed by the present invention. HSV-2 contains both RR subunits; HSV-1 ICP6 is analogous to HSV-2 ICP10. Nikas et al., *Proteins* 1: 376 (1986); McLaughlan and Clements, EMBO J. 2: 1953 (1983); Swain and Halloway, *J. Virol.* 57: 802 (1986). $\gamma 34.5$ is also present in HSV-2. McGeoch et al., *J. Gen. Virol.* 72: 3057 (1991).

Impairment of Gene Expression Via Modification of $\gamma 34.5$ or Ribonucleotide Reductase Regulatory Sequences Another way to render a herpes simplex virus incapable of expressing functional $\gamma 34.5$ gene product and ribonucleotide reductase is to impair their expression. The expression of these two genes can be halted by altering the regulatory sequences of the $\gamma 34.5$ and ribonucleotide reductase genes.

The regulatory regions for $\gamma 34.5$ and/or ribonucleotide reductase can be altered by standard techniques to disrupt the expression of the $\gamma 34.5$ and ribonucleotide reductase gene. For example, their regulatory sequences could be altered within the viral genome using techniques described above for the alteration of coding sequences.

The promoter regions of $\gamma 34.5$ and ribonucleotide reductase ICP6 have been mapped. The promoter for $\gamma 34.5$ has been mapped to a region within the "a" sequence. The "a" sequence also contains sequences for cleavage of unit length DNA from HSV-1 concatamers, packaging of HSV-1 DNA into capsids and inversion of L and S components. Chou and Roizman, *J. Virol.* 57: 629 (1986). The promoter region of ICP6 has been mapped to the 5' upstream sequences of the ICP6 structural gene. Goldstein and Weller, *J. Virol.* 62: 196 (1988); Sze and Herman, *Virus Res.* 26: 141 (1992). The transcription start site for the small subunit of RR, namely UL40, falls within the coding region of ICP6. McLauchlan and Clements, *J. Gen. Virol.* 64: 997 (1983); McGeoch et al., *J. Gen. Virol.* 69: 1531 (1988).

The effect of these alterations on the regulatory capacity of $\gamma 34.5$ and RR genes can be detected by inserting a reporter gene downstream of the promoter, such as that described for the ICP6/lacZ fusion. Goldstein and Weller, *J. Virol.* 62: 196 (1988); Sze and Herman, *Virus Res.* 26: 141 (1992). Because herpes simplex virus genes are regulated differently when present in the cellular genome, the effects of each alteration in the $\gamma 34.5$ or ribonucleotide reductase regulatory component would be assessed in various mammalian target cells. McKnight et al., in CANCER CELLS 4; DNA TUMOR VIRUSES, Cold Spring Harbor (1986) 163–173.

Additional methods for the construction of engineered viruses are known in the art. Additional methods for the genetic manipulation of DNA sequences are known in the art. Generally, these include Ausubel et al., chapter 16 in CURRENT PROTOCOLS IN MOLECULARBIOLOGY (John Wiley and Sons, Inc.); Paoletti et al., U.S. Pat. No. 4,603,112 (July 1986). Virological considerations also are reviewed in Coen D. M., "Molecular Genetics of Animal Viruses," in VIROLOGY 123–150 (2nd ed.) (Raven Press, 1990).

The construction of HSV-1 vectors is described, for example, in U.S. Pat. No. 5,288, 641; Roizman and Jenkins, J. Science 229: 1208 (1985); Johnson et al., J. Virol. 66: 2952 (1992); Gage et al., J. Virol. 66: 5509 (1992); Spaete and Frenkel, Cell 30; 295 (1982); Goldstein and Weller, J. Virol. 62: 196 (1988), Coen, chapter 7, Virology, Raven Press, 1990; Breakefield and DeLuca, The New Biologist, 3: 203 (1991); Leib and Olivo, BioEssays 15: 547 (1993); Glorioso et al., Seminars in Virology 3: 265 (1992); Chou and Roizman, Proc. Natl. Acad. Sci. USA, 89: 3266 (1992); Breakfield et al., Molec. Neurobiol. 1: 339 (1987); Shih et al., in: VACCINES 85, Cold Spring Harbor Press (1985) 177–180; Palella et al., Molec. Cell. Biol. 8: 457 (1988); Matz et al., J. Gen. Virol. 64: 2261 (1983); Mocarski et al., Cell 22: 243 (1980); and Coen et al., Science 234: 53 (1986).

Imparting Hypersensitivity to Antiviral Agents

One safety precaution in the therapeutic use of herpes simplex virus against gliomas involves providing a means to stop any potential infection of other dividing cells. Clinical studies indicate that even wild-type HSV-1 viruses generally do not spread far from the site of initial infection or cause serious systemic disease in immunocompetent individuals. Sacks et al., Ann. Int'l Med. 111: 893 (1989).

It is noted that TK$^-$ viruses have sometimes been associated with progressive disease in certain immunocompromised patients and that the HSV-1 mutant dlsptk is resistant to acyclovir. Erlich et al., New Engl. J. Med. 320: 293 (1989); Coen et al., Proc. Nat'l Acad. Sci. USA 86: 4736 (1989). Any mutant replication-competent viral vector that is more sensitive to the anti-viral agent than its wild-type parent is deemed hypersensitive to the anti-viral agent, potentially providing a means to abort an undesired spread of the mutant virus.

In constructing herpes simplex virus mutants for use in vivo, the mutants are tested for their sensitivity to current anti-herpetic drug therapies in order to control unforeseen virulent infections. A number of drugs currently are available to treat herpes infections in humans, the most effective being nucleoside analogs which block herpes simplex virus DNA replication. Three herpes simplex virus genes are known to be involved in sensitivity to nucleoside analogs: herpes simplex virus DNA polymerase (UL30, pol), herpes simplex virus thymidine kinase (UL23,tk), and CMV UL97 which shares homology with protein kinases and bacterial phosphotransferases. Furman et al., J. Virol. 32: 77 (1979); Littler et al., Nature 358: 160 (1992); Sullivan et al., Nature 358: 162 (1992).

There are a number of herpes simplex virus DNA polymerase mutants which exhibit hypersensitivity to ganciclovir, including PAA$^r$5 and AraA$^r$9. Coen et al., J. Virol. 53: 477 (1985). Unfortunately, intracranial injections of AraA$^r$9 led to premature death and had no effect on subcutaneous tumor growth. Markert et al., supra. Another mutant herpes simplex virus, the dlsptk virus, is no longer drug sensitive, at least to nucleoside analog drugs, and therefore potentially uncontrollable in vivo.

Attenuation for Neurovirulence

Attenuated or decreased generalized neurovirulence means that life-threatening encephalitis does not ensue after infection with the double mutant herpes simplex virus vector of the instant invention. Because herpes simplex virus-induced encephalitis in humans is very difficult to treat and can be fatal, even with adequate pharmacologic measures, decreased generalized neurovirulence is an important feature of the instant invention. The mutant virus of the present invention is capable of replicating in neoplastic cells but spares surrounding non-neoplastic tissue.

Different herpes simplex virus strains vary in neurovirulence and more attenuated strains may be employed in the construction of the double mutant to further decrease neurovirulence. Other HSV-1 strains available from ATCC include HF (ATCC VR-260), MacIntyre (ATCC VR-539), MP (ATCC VR-735) and HSV-2 strains G (ATCC VR-734) and MS (ATCC VR-540).

Alternatively, any herpes simplex virus gene mutation leading to decreased viral replication in vivo and/or in specific cell populations may be used in the mutated herpes simplex virus vector of the invention. Other neurovirulence genes include: (i) dUTPase [Pyles et al., J. Virol. 66: 6706, (1992)], (ii) UL53 [Moyal et al., Virus Res. 26: 99 (1992)], (iii) α22 [Sears et al., J. Virol. 55: 338 (1985)] and (iv) US3 [Meignier et al., Virology 162: 251 (1988)].

From a clinical perspective, herpes simplex virus encephalitis is the most commonly reported viral infection of the central nervous system (CNS) in the United States, with an estimated incidence of 2.3 cases per million population. Herpes simplex virus encephalitis is usually localized to the temporal lobe and the limbic system and histological examination of autopsy cases demonstrates viral antigen at these sites. A number of drugs are available to control infection, including acyclovir 9-92-hydroxyethoxy-methyl)guanine, Zovirax®, adenine arabinoside (Vidarabine®), foscarnet (phosphonoformic acid, PFA) and ganciclovir 9(1, 3-dehydroxy-2-propoxy)methylguanine, DHPG, 2'NDG, Cytovene®. See Whitley et al., in Lopez et al., (eds.) IMMUNOBIOLOGY AND PROPHYLAXIS OF HUMAN HERPESVIRUS INFECTIONS, page 243 (1990, Plenum Press, N.Y.); Whitley et al., N. Engl. J. Med. 297: 289 (1977); Oberg, Pharmacol. Ther. 19: 387 (1983); DeArmond, Transplant. Proc. 23: 171 (1991).

Achieving Tumor-Specificity

Because herpes simplex virus has a very broad host range and seems capable of infecting all cell types in the CNS, herpes simplex virus mutants of the instant invention may be targeted to specific tumor types using tumor cell-specific promoters. The term "tumor cell-specific promoter" indicates a promoter that is induced selectively or at a higher level in the target tumor cell than in a normal cell. Tumor cell-specific promoters include promoters that are induced selectively or at a higher level in a particular cell type or a tumor cell.

The vectors of the invention also can be designed to selectively replicate in and kill a tumor cell of non-nervous tissue origin. The herpes simplex virus vector of the invention is engineered to place at least one viral protein necessary for viral replication under the control of a cell specific or tumor cell-specific promoter. The tumor cell-specific promoter is induced selectively or at higher levels in tumor cells than in normal cells.

Such tumor cell-specific, HSV-1 mutants utilize promoters from genes that are highly expressed in the targeted tumor, such as the epidermal growth factor receptor gene promoter (EGFr) or the basic fibroblast growth factor (bFGF) gene promoter or the NESTIN or other tumor associated promoters or enhancer elements to drive expression of an essential herpes simplex virus gene (e.g., ICP4), under circumstances in which the wild-type essential herpes simplex virus gene would not be expressed. Rendering the essential herpes simplex virus gene non-functional can be achieved by genetic inactivation or replacement of promoter with tumor cell-specific promoter.

The instant invention encompasses a host-range conditional herpes simplex virus mutant where an essential viral gene product is under the control of a tumor cell-specific promoter rather than its own viral promoter. In permissive cells, containing the proper regulatory proteins for this specific promoter, the essential viral gene product is expressed and the virus is able to replicate and spread to adjacent cells until a non-permissive cell is infected. These studies are applicable to the replication-competent herpes simplex virus of this invention. These constructs, however, are only replication-competent in the correct cell types (i.e., tumor cells) and are replication-deficient in other cells (i.e., surrounding tissue).

Many tumor cell types express phenotypic markers which are turned off in the normal, terminally-differentiated cell. One can take advantage of this altered expression pattern to construct tumor cell-specific viruses. Examples of such differentially regulated genes in neural tumors include: (i) nestin, an intermediate filament protein normally expressed in neuroepithelial stem cells, yet not in mature CNS cells, which is ubiquitously expressed in human brain tumors, most prominently in gliomas, (ii) basic fibroblast growth factor (bFGF), a differentiation factor and mitogen for neuroectoderm, which is highly expressed in human gliomas and meningiomas but not in metastatic brain tumors or normal brain tissue and (iii) epidermal growth factor receptor (EGFr), a membrane-bound tyrosine-specific protein kinase that is stimulated by EGF, which is very often overexpressed, altered and the gene amplified in human high grade gliomas but rarely in normal brain.

Herpes Simplex Virus Vectors Effective for Xenogenization

The mutant herpes simplex virus vector of the instant invention can be employed in a genetic therapy against specific tumors by expressing foreign genes in a tumor cell-specific fashion in order to target an immune response that kills the tumor cells. Tepper and Mulé, *Human Gene Therapy* 5: 153 (1994). In addition, the instant invention employs the replication competent herpes simplex virus vector having decreased neurovirulence as a tumor cell modulator or inducer of an immune response against the tumor cells. The mutant herpes simplex virus vector of the invention can be further altered to express cytokines in the tumor target cell in order to elicit an immune response against the tumor cells. For example, a mutant herpes simplex virus vector can induce viral-mediated killing of tumor cells, which then is amplified by a cytokine-enhanced immune response, a cytokine having been expressed by the vector itself. The expression of cytokines, or other gene products, from the mutant herpes simplex virus vector would occur within hours of infection so that sufficient gene products would be synthesized prior to cell killing. Cell killing may even increase the efficacy of the anti-tumor immune response. Barba et al., *Proc. Nat'l Acad. Sci. USA* 91: 4348 (1994).

Herpes Simplex Virus Vector-Mediated Destruction of Tumor Cells

Exemplary candidates for treatment according to the present invention include, but are not limited to (i) non-human animals suffering from tumors and neoplasms, (ii) humans suffering from tumors and neoplasms, (iii) animals suffering from nervous system tumors and (iv) patients having malignant brain tumor, including astrocytoma, oligodendroglioma, meningioma, neurofibroma, glioblastoma, ependymoma, Schwannoma, neurofibrosarcoma, and medulloblastoma.

Preferentially, the treatment will be initiated by direct intraneoplastic inoculation. For tumors in the brain, MRI, CT, or other imaging guided stereotactic technique will be used to direct viral inoculation or virus will be inoculated at the time of craniotomy.

The pharmaceutical compositions of the present invention would be advantageously administered in the form of injectable compositions. A typical composition for such purpose would comprise a pharmaceutically acceptable vehicle. For instance, the composition could contain human serum albumin in a phosphate buffer containing NaCl. Other pharmaceutically acceptable carriers include aqueous solutions, non-toxic excipients, including salts, preservatives, buffers and the like. See REMINGTON'S PHARMACEUTICAL SCIENCES (15th ed.) 1405–1412 & 1461–1487, Mack Publishing Co. (1975), and THE NATIONAL FORMULARY XIV (14th ed.), American Pharmaceutical Association (1975). Examples of non-aqueous solvents are propylene glycol, polyethylene glycol, vegetable oil and injectable organic esters such as ethyloleate. Aqueous carriers include water, aqueous solutions, saline solutions, parenteral vehicles such as sodium chloride, Ringer's dextrose, etc. Intravenous vehicles include fluid and nutrient replenishers. The pH and exact concentration of the various components the pharmaceutical composition are adjusted according to routine skills in the art. Goodman and Gilman, THE PHARMACOLOGICAL BASIS FOR THERAPEUTICS (7th ed.).

Typically, the herpes simplex virus vector would be prepared as injectables, either as liquid solutions or suspensions; solid forms suitable for solution in, or suspension in, liquid prior to injection may also be prepared. The preparation also may be emulsified. The active immunogenic ingredient is often mixed with an excipient which is pharmaceutically-acceptable and compatible with the active ingredient. Suitable excipients are, for example, water, saline, dextrose, glycerol, ethanol, or the like and combinations thereof. In addition, if desired, the vector may contain minor amounts of auxiliary substances such as wetting or emulsifying agents, pH-buffering agents, adjuvants or immunopotentiators which enhance the effectiveness of the vector vaccine.

Additional formulations which are suitable for other modes of administration include oral formulations. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders and contain 10%–95% of active ingredient, preferably 25–70%.

The term "unit dose" refers to physically discrete units suitable for use in humans, each unit containing a predetermined quantity of active material calculated to produce the desired therapeutic effect in association with the required diluent, i.e., carrier or vehicle, and a particular treatment regimen. The quantity to be administered, both according to number of treatments and amount, depends on the subject to be treated, capacity of the subject's immune system to synthesize antibodies, and degree of protection desired. Precise amounts of active ingredient required to be administered depend on the judgment of the practitioner and are peculiar to each individual. However, suitable dosage ranges are on the order of one to several hundred micrograms of active ingredient per individual. Suitable regimes for initial administration and booster shots also vary but are typified by an initial administration followed in one or two week intervals by one or more subsequent injections or other administration.

EXAMPLE 1

CONSTRUCTION OF HIGHLY ATTENUATED, DOUBLE HSV MUTANTS

Viruses and Cell Lines

HSV-1 wild-type strain (KOS or Strain F) and HSV mutants (R3616, hrR3) were kindly provided by D. M. Coen, B. Roizman, J. Chou, and S. K. Weller. HSV-1 strain F is available as ATCC VR-733; Vero cells are available as ATCC CRL 1587. R3616, which is derived from HSV-1 strain F, contains a 1-kilobase-pair deletion in both copies of the $_\gamma 34.5$ gene. R3616 was constructed as described in Chou et al., Science 250: 1262 (1990).

Stocks of viruses were generated in African green monkey kidney cell (Vero) cultures as described. Virus stocks were prepared as described by Coen et al., J. Virol. 53: 477 (1985).

Human glioblastoma cells U-87MG, T98G, U-138MG, and A172 were obtained from American Type Culture Collection (Rockville, Md.) and cultured in Dulbecco's minimal essential medium (DMEM) supplemented with 10% inactivated fetal calf serum (IFCS) and antibiotics.

Viral DNA is isolated from infected cells, which are gently lysed with NP40, treated with RNase, then SDS and Proteinase K, and finally extracted with phenol, chloroform/isoamylalcohol, and ether. The viral DNA is suitable for transfection after precipitation with ethanol and resuspension in water. For the generation of recombinant viruses, the piece of DNA to be recombined into the viral genome is excised from a plasmid. The linear DNA is co-transfected with viral DNA into cells capable of supporting propagation of the recombinant progeny virus. When extensive cytopathic effects are observed, progeny virus is harvested. Recombinant viruses are then plated on permissive cells under selectable or screenable conditions. For example, LacZ+ recombinant plaques are stained by adding X-gal and blue plaques (LacZ+) are selected. Further plaque purification (three times) is conducted before a stock is made.

Construction of Herpes Simplex Virus Incapable of Expressing Both $_\gamma 34.5$ Gene Product and Ribonucleotide Reductase Herpes simplex virus strains mutated in both the $_\gamma 34.5$ and ribonucleotide reductase genes are constructed using standard procedures for the generation of viral recombinants as described by Goldstein and Weller. Both of these genes are non-essential for viral growth in culture and therefore null mutants are viable in culture. Such double mutants include the insertion of the E. coli Lac Z gene in either gene, so that replication in site can readily be detected.

An exemplary mutant herpes simplex virus vector of the instant invention can be constructed by homologous recombination using DNA isolated from R3616 virus and a 5.3 kB HindIII-XbaI fragment of pKX2-βG3. One example of such a mutant within the present invention is designated "G207." FIG. 1 illustrates the construction of G207. Five isolates were purified and termed G207-1, -2, -3, -4, -5.

The HSV-1 mutant R3616, derived from HSV-1 wild-type strain F, contains a 1-kB deletion in both copies of the $_\gamma 34.5$ gene. To construct an ICP6 lacZ insertion in R3616 viral DNA, the 5.3 kb HindIII-XbaI fragment of pKX2-βG3, which contains a lacZ insertion in the 2.3-kB XhoI fragment of ICP6 gene, was cotransfected with R3616 infectious viral DNA into Rabbit Skin (RS) cells, and introduced into the viral DNA by homologous recombination. Plasmid pKX2-βG3 containing a lacZ gene insertion in the 2.3 Kb XhoI fragment of ICP6 gene (KOS), was kindly provided by Dr. S. K. Weller (Univ. of Connecticut). Goldstein and Weller, J. Virol. 62: 196 (1988). Plasmid pKpX2' was constructed by partial digestion of pKX2-βG3 with BamHI, removal of lacZ gene and religation. Plasmid pRB4081 containing NcoI-SphI fragment of $_\gamma 34.5$ gene, was kindly provided by B. Roizman. Chou et al., Science 25: 1262 (1990). All recombinant plasmids were propagated by standard procedures.

Two hundred to 1,000 infectious units of R3616 viral DNA (approximately 1 μg) are co-transfected with a 10-fold molar excess of the 5.3 kB insert of pKX2-βG3, which is excised by cutting with XbaI and HindIII, to RS cells. When wide spread cytopathic effects were observed, progeny are harvested and titers determined on Vero cells.

On day 2 or 3 following infection, plaques were stained with X-gal solution. Recombinant viruses were identified by plaques staining positive with X-gal. Recombinant viral plaques ($_\gamma 34.5$-/ICP6- and LacZ$^+$) stain blue in the presence of X-gal. Recombinant virus from blue plaques is purified and the DNA analyzed by restriction endonuclease mapping to confirm the DNA structure of the mutant viruses. Blue plaques were purified three times by passage in Vero cells in a limiting dilution method before stocks were made.

The plaque morphology of G207-1 and G207-2 was analyzed as well as the effect of various concentrations of IFCS-containing medium on plaque morphology. Infected vero cell monolayers were cultured at 37° C. in medium containing 0.5%, 1%, 2.5% and 5% IFCS; were fixed at 36–48 hr post-infection; and were stained with X-gal, to detect β-gal activity, and then counterstained with neutral red.

G207-1 mutants produced non-syncytial plaques, whereas G207-2 mutants produced syncytial plaques, characterized by extensive cell-cell fusion.

Table 1 documents the increasing plaque diameters under conditions of increased cell growth for G207-1 and G207-2. The diameters of plaques were measured using a micrometer under an inverted phase-contrast microscope at 40X magnification. Each value represents the average diameter of 15 plaques.

TABLE 1

| Diameters of plaques in various concentrations of IFCS medium | | | |
|---|---|---|---|
| | 0.5% IFCS | 1% IFCS | 5% IFCS |
| R3616 | 0.48 ± 0.13 | 0.44 ± 0.12 | 0.45 ± 0.094 (NS) |
| | | | 1.1 ± 0.36 (Syn) |
| G207-1 (Non-syn.) | 0.42 ± 0.15 | 0.48 ± 0.16 | 0.63 ± 0.18 |
| G207-2 (Syn.) | 0.45 ± 0.16 | 0.48 ± 0.17 | 1.0 ± 0.30 |
| (mm: mean ± SD) | | | |

Figure 2:
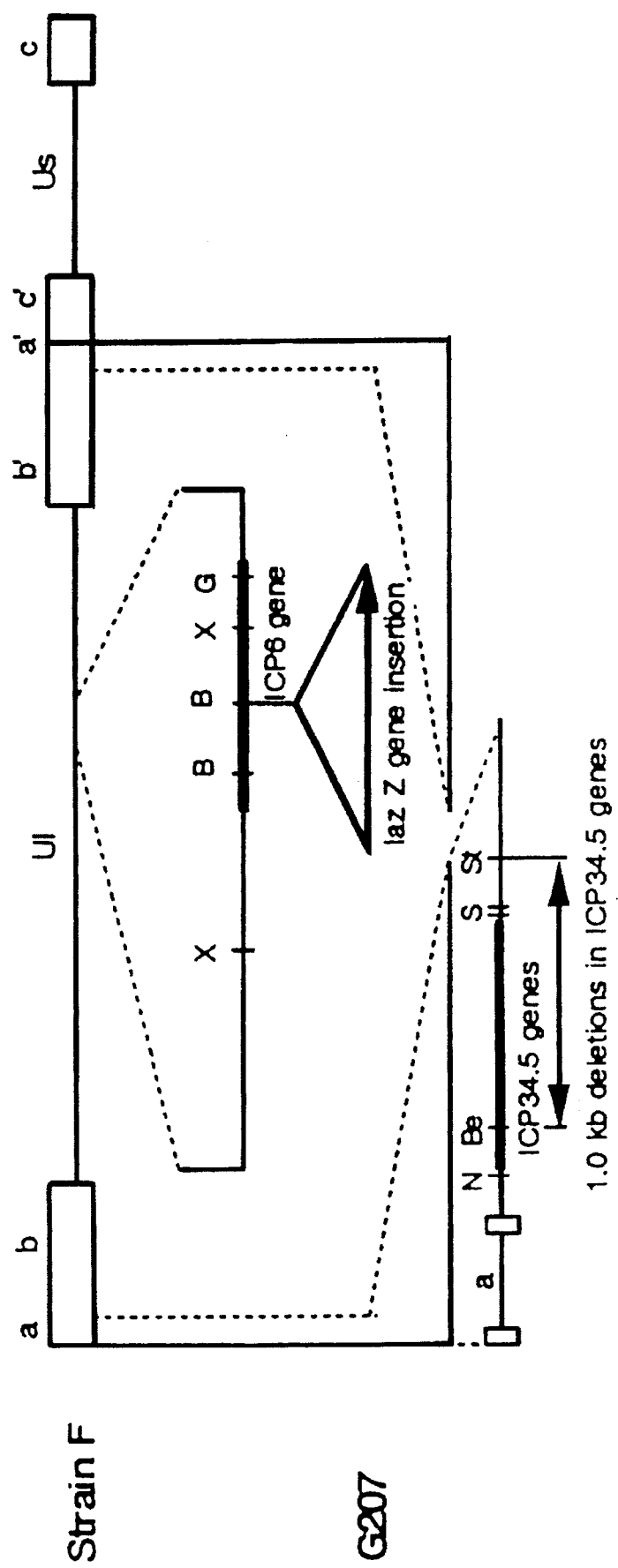
FIG. 2 shows the sequence arrangement of a mutant herpes simplex virus, G207-1, compared to its parental wild-type background (strain F). The abbreviations are B, BamHI; Bc, BstEII; G, BglIII; N, NcoI; S, ScaI; St, StuI; and X, XhoI.

The sequence and gene arrangement of G207 viruses compared to its strain F wild-type background is illustrated in FIG. 2. The boxes on FIG. 2's top line represent the inverted repeat sequence flanking the long ($U_L$) and short (Us) components of herpes simplex virus genome, which is represented by thin lines. The expanded domains of the long unique region show the location of the ICP6 gene. The thick line shows the transcribed sequences of ICP6 gene. Mutant G207 contains the structural gene of lacZ inserted into the BamHI site in the ICP6 gene. The expanded domains of the repeat regions show the location of the $\gamma 34.5$ gene. Mutant G207 contains a 1 kB deletion in both copies of the $\gamma 34.5$ gene.

Analysis of Mutant Viral DNA

In order to confirm the correctly altered structure of the herpes simplex virus vectors, Southern blot analysis was performed on the mutants of invention. Viral DNAs were prepared from partially purified virions. Total viral DNAs (KOS, hrR3, Strain F, R3616, and G207) were digested with restriction endonuclease, separated by agarose gel electrophoresis in a Tris-borate-EDTA buffer and transferred by the method of Southern. Recombinant DNAs used as probes for hybridization were labeled by ECL labeling Kit (Amersham) as suggested by the supplier. To confirm that the viral mutants contain the lacZ gene at the appropriate position, total DNA was digested with Xho I and subjected Southern blot hybridization in duplicate. Filters were hybridized with labeled pkpX2', which contains wild-type sequences of ICP6 gene. HSV-1 wild-type KOS contains a wild-type 2.3 kB Xho I fragment, whereas, hrR3 (KOS derived and lacZ insertion mutant in ICP6 gene) contains the 5.3 kB fragment expected if the lacZ gene was inserted. HSV-1 strain F contains an approximately 6.0 kB Xho I fragment due to a polymorphism between herpes simplex virus wild-type strains. G207 contains a 9.0 kB fragment, expected if the lac Z gene was inserted into the 6.0 kB fragment of strain F. When the filter was hybridized with a lacZ gene probe alone, only the 5.3 kB fragment of hrR3 and the 9.0 kB fragment of G207 was detected. These results demonstrates that the lac Z gene fragment is inserted into appropriate site in the genome.

To confirm that G207 contains deletions in the $\gamma 34.5$ gene. Viral DNAs of strain F, R3616, G207 were digested with Bam HI and subjected to Southern blot hybridization. Plasmid pRB4081, containing wild-type sequences of the $\gamma 34.5$ gene was used as probe. The $\gamma 34.5$ gene maps in the Bam HI SP and S fragments. Strain F contains the wild-type Bam HI SP and S versions of these fragments, whereas R3616 and G207 contain the deleted versions of these fragments. These results demonstrate that both $\gamma 34.5$ genes are deleted in R3616 and G207 viral DNA.

Herpes Simplex Virus Mutants Targeted to Specific Cell Types

Plasmids containing the 2.2-kB EGFR promoter fragment from pERCAT2, see Johnson et al., *J. Biol. Chem.* 263: 5693 (1988), and a 2.1-kB BFGF promoter fragment from pF2.ICAT, see Shibata et al., *Growth Factor* 4: 277 (1991), are used to characterize transient expression of a marker protein (β-galactosidase). The cell-specificity of these constructs is confirmed in human U-87MG glioblastoma cells for BFGF [Takahashi et al., *FEBS Letters* 288: 65 (1991)] and in A431 human epidermoid carcinoma cells for EGFR. Liberman et al., *Nature* 313: 144 (1985). A431 cells are available as ATCC: CRL 1555; U-87MG MG cells are available as ATCC: HTB 14.

For example, the tumor cell-specific promoter is cloned into an ICP4 plasmid upstream of the ICP4 coding region. Examples of ICP4 plasmids include pGH108 or pXhoI-C. Roberts et al., *J. Virol.* 62: 4307 (1988). This plasmid is then recombined into herpes simplex virus ICP4$^-$. Herpes simplex virus ICP$^-$ can be constructed by deletions or insertions into the ICP4 coding region. DeLuca et al., *J. Virol.* 56: 558 (1985); DeLuca and Schaffer, *Nucleic Acids Res.* 15: 4491 (1987); Paterson and Everett, *J. Gen. Virol.* 71: 1775 (1990). The vector of the invention can also be made ICP4- by a deletion or insertion into the ICP4 coding region. Such ICP4$^-$ vectors are isolated on ICP4 expressing cells. DeLuca et al., supra; DeLuca and Schaffer, supra; Paterson and Everett, supra. Alternatively, the ICP4 regulatory region of the herpes simplex virus vector is replaced with the tumor cell-specific promoter so that ICP4 is only produced in cells capable of expressing the replaced promoter. The herpes simplex virus mutant containing its ICP4 gene under the control of a tumor cell-specific promoter is tested for its ability to infect and kill specific tumor cells.

EXAMPLE 2

SAFETY AND EFFICACY STUDIES

The in vitro efficacy of the mutants as anti-glioma agents can be determined using assays of glioma cytotoxicity on cultures of a long-term human glioma cell line, U-87MG, as well as early-passage human glioblastomas. To evaluate tumor inhibition in vivo, subcutaneous U-87MG xenografts in nude mice are treated separately with inoculations of each viral mutant or vehicle, and tumor growth rates were analyzed. To investigate the potential effects of the herpes simplex virus mutant treatment on survival, nude mice with intracranial U-87MG xenografts are treated with virus or vehicle inoculations, and overall survival is compared.

To evaluate the degree of tumor eradication, as well as the potentially retained neurovirulence of the viruses when used at doses necessary to achieve prolonged survival, the brains of long-term survivors with intracranial xenografts are sectioned, stained, and microscopically examined. For effective in vivo tumor inhibition and survival prolongation, careful choice of mutant employing the assays described herein is essential. The following methods provide clear guidance to those of skill in the art to screen for mutant viral vectors that are effective in vivo in inhibiting tumor growth and prolonging survival. To establish the relative safety of these viruses as potential anti-glioma agents, their susceptibility to the common antiherpetic agent ganciclovir is investigated. Finally, to establish the safety of intracerebral inoculation of the mutant viral vector, animals receive an intracerebral inoculum of the mutant virus and are subsequently assessed for encephalitis.

In vitro Cytopathic Killing

The ability of the herpes simplex virus vectors of the invention to kill tumor cells is first tested in cell culture. All viral work is done in approved, designated viral vector rooms. Viruses are initially grown on Vero cells, as described in Martuza et al., *Science* 252: 854 (1991). To maximize the titer of the viral mutant, the initial viral suspension was centrifuged at 34,500 g for 2 h at 4° C., and the pellet was subsequently suspended in media and again titered. Viruses are applied at varying multiplicities of infection (MOIs), between $10^1$ and $10^{-4}$. MOI values were calculated from cell number. The appropriate number of viral pfu was applied and distributed evenly. Coen et al., *J. Virol.* 53: 477 (1985). All viral-infected cell cultures were compared with control cultures (DMEM+ only, no virus). Cells were maintained and observed microscopically. Cells that had become rounded, losing normal morphology, and those lifting from the plate were considered dead. Monolayers were considered completely destroyed when 99% or more of the cells exhibited such cytopathic effects.

Either the mutant or its wild-type parent were applied to a human glioma line (U-87MG) and African green monkey kidney (Vero) cells at multiplicities of infection (MOIs) from $10^{-4}$ to $10^1$ in DME+ (Dulbecco's modified Eagle's medium with 1–5% heat-inactivated fetal calf serum (IFCS) and antibiotics). The malignant human glioma line U-87MG was obtained from American Tissue Cell Collection, Rockville, Md. Additionally, two primary human malignant gliomas were obtained as surgical tumor specimens. Martuza et al., supra, (1991). All cells were grown in Dulbecco's modified Eagle's medium with 10% fetal bovine serum and antibiotics (DMEM+).

Subconfluent monolayers of U-87MG and Vero cells were infected with the mutant viral vectors of the invention at varying MOIs. The infected cells are cultured in 1–5% IFCS-containing medium at 34.5° C. The viable cells were identified by the Trypan blue exclusion method. The mutant expressing cytopathic effects at 24 hours that is proportional to the MOI and expressing >99% cytopathic effect after 10 days in U-87MG is deemed to possess the ability to kill glioma cells in vitro. The lowest inoculum of the mutant virus that can sustain a spreading infection to destroy the entire monolayer of U-87MG cells will provide one of the doses at which the mutant is evaluated in vivo. The mutant viral vector also is tested against a different human glioma line (T98G) at various MOIs and assessed for its ability to produce monolayer destruction within 10 days.

Short-term glioma cultures were established by explanting three malignant human gliomas (one anaplastic astrocytoma and two glioblastomas) obtained at surgery in DME+ and were studied at the second passage. The mutants are tested at various MOIs for their cytopathic effects. The herpes simplex virus mutant and dose that is cytopathic in all three primary malignant gliomas is deemed to be able to kill a wide variety of human brain tumor cells in vitro.

In addition to glioma cultures, the viral mutants are tested for their ability to kill 3 human malignant meningiomas, 1 atypical meningioma, 5 neurofibrosarcomas, and 2 medulloblastomas in cell culture, and in the in vivo models. The viral mutants are tested at MOIs ranging from $10^1$ to $10^{-4}$. Significant tumor inhibition by the mutant virus reveals a wide range of nervous system tumors for which the viral mutant is efficacious in killing human brain tumor cells.

Figure 3:
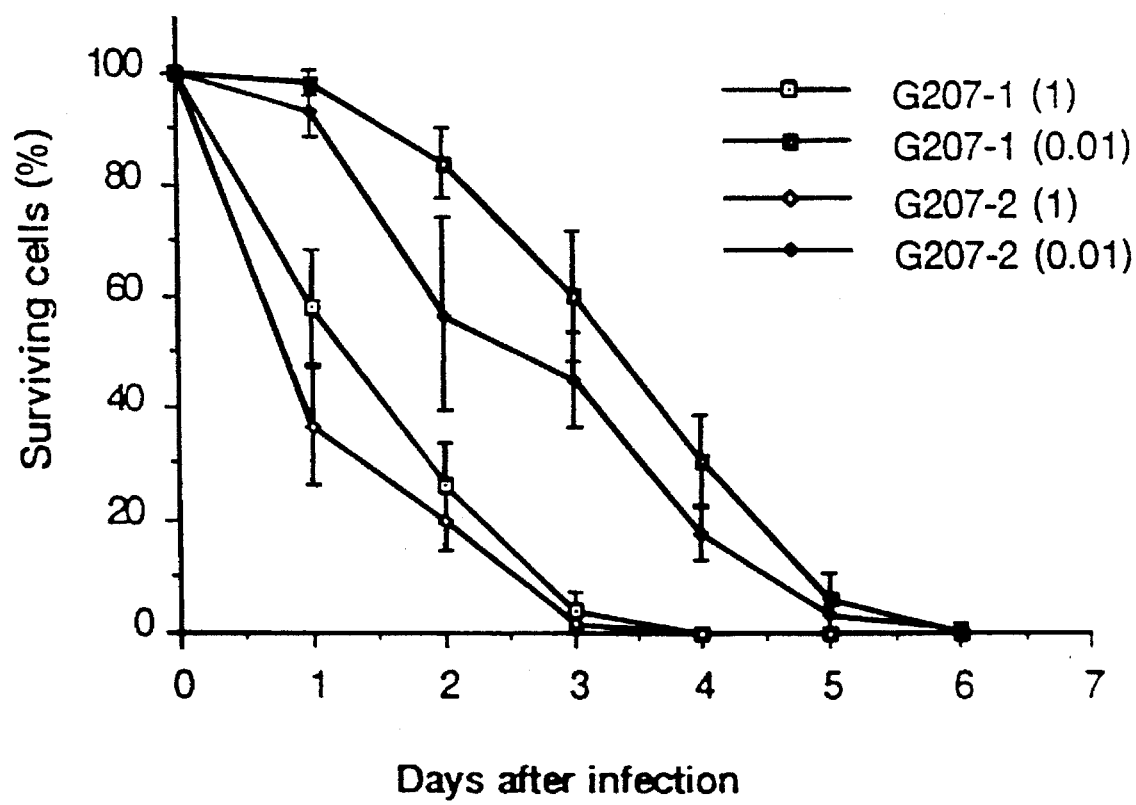
FIG. 3 is a graph illustrating the ability of G207-1 and G207-2 to kill all human U-87MG glioma cells in culture, including at low multiplicity of infection (MOI=0.01).

FIG. 3 documents the in vitro cytopathic efficacy of G207-1 and G207-2 on U-87MG cells. Subconfluent monolayers of U-87MG cells were infected with G207-1 or G207-2 (MOI=0.01 or 1), while the controls were mock-infected and cultured with 10% IFCS-containing medium at 34.5° C. The viable cells were identified by the Trypan blue exclusion method. The number of surviving cells relative to the number of cells in mock-infected control cultures (100%) was assessed. Each data point represents the mean of triplicates. Vertical bars indicate the standard deviation of the triplicates. Each of the viral mutants killed all of the tumor cells by 6 days postinfection. Cytopathic effect appeared on day 1 postinfection for MOI of 1.0, with >99% cytotoxicity evident by day 3 for 1.0 MOI and by day 6 for 0.01 MOI. The cytopathic efficacy of these mutants can also be tested on the human glioma cells lines T98G, U-138MG and A172.

The herpes simplex virus vector of the instant invention can be used to mediate the destruction of other human tumors. Examples of other human tumors that may be amenable to this invention include melanoma, carcinoma of the prostate, breast cancer, pancreatic cancer, lung cancer, colon cancer, lymphoma, hepatoma, and mesothelioma. Human tumor cells can be cultured from primary tumors as described. Fogh and Trempe, HUMAN TUMOR CELLS IN VITRO, Plenum Press, N.Y. (1975) p. 115; Wilson, chapter 8, ANIMAL CELL CULTURE, A PRACTICAL APPROACH. IRL Press (1986). We have shown that a human melanoma cell line, SK-MEL-31 (ATCC: HTB 73); human prostate carcinoma cell lines, Du145 (ATCC: HTB 81) and PC3 (ATCC: CRL 1435); human epidermoid carcinoma cells, A431 (ATCC: CRL 1555); and human lung carcinoma cells, Calu-1 (ATCC: HTB54) are susceptible to infection by attenuated mutants of HSV-1.

Anti-viral Agent Sensitivity

To overcome the insensitivity of some of the prior art herpes simplex virus mutants to anti-viral agents, another drug target (for example, suicide-gene) is inserted into the virus. For example, the CMV UL97 gene ($gan^S$; pGMT7-UL97) is inserted into TK$^-$ HSV-1 mutants and tested for its ability to complement the inability of TK$^-$ HSV-1 to replicate in serum-starved cells and confer ganciclovir sensitivity on this recombinant. After the viral vector containing the suicide gene is tested for ganciclovir sensitivity, a comparison of the $ED_{50}$ (in vitro) and Mean Survival Time of the suicide containing and suicide absent viral vectors (e.g. HSV-1 mutants TK$^-$/UL97 and dlsptk) is made in the presence of ganciclovir.

Ganciclovir-sensitivity Assay

Figure 4:
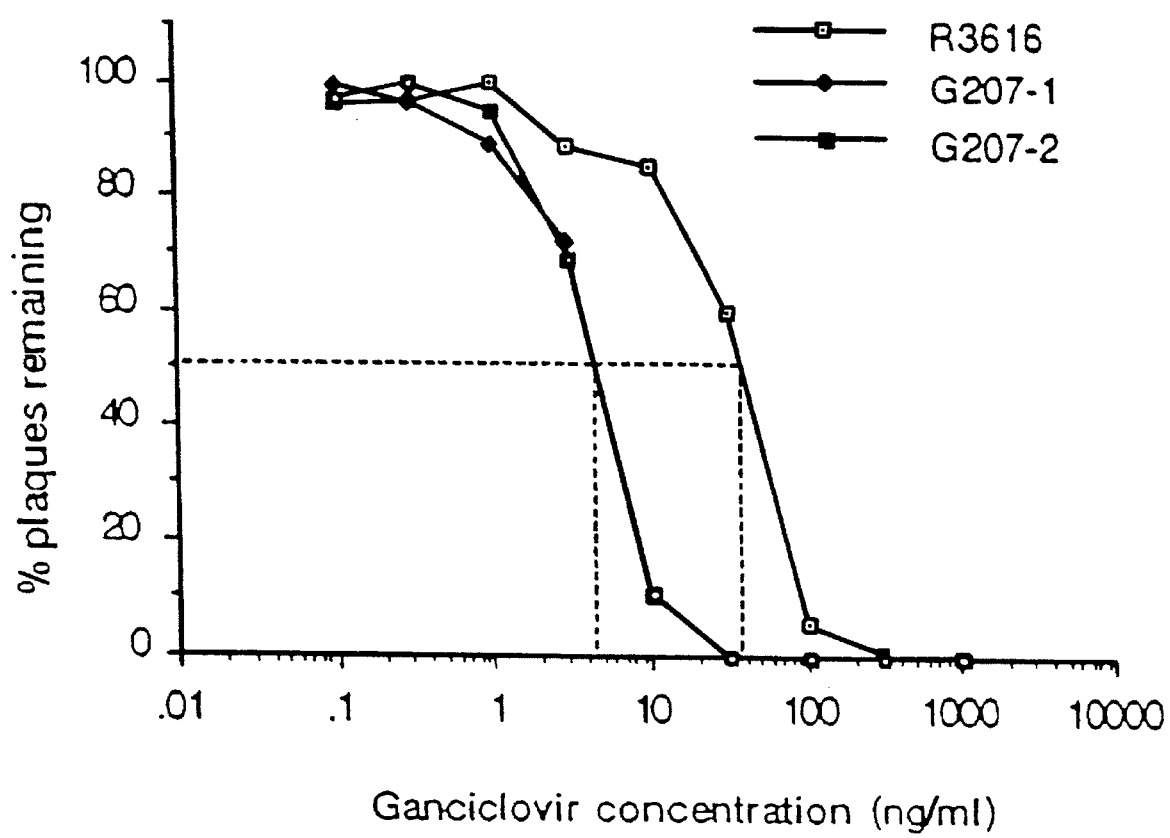
FIG. 4 is a graph illustrating the ganciclovir (GCV) sensitivity of R3616, G207-1, and G207-2 which reveals that G207-1 and G207-2 are ten-times more sensitive to ganciclovir than R3616. R3616 (strain F) has the same sensitivity to ganciclovir as strain KOS (wild-type).

Confluent monolayers of Vero cells in 12-well plates are infected with 100 pfu of R3616 or G207, where the MOI remains below 0.0005. After removing the virus inoculum, DMEM plus 1% inactivated fetal calf serum and 1000-fold diluted human immunoglobulin (Armour Pharmaceutical Company; Kankakee, Ill.) containing various concentrations of ganciclovir is added to triplicate cultures and cells are incubated at 37° C. Plaques are visualized by Giemsa stain and counted on day 3 postinfection. The ganciclovir (GCV) sensitivity of R3616, G207-1, and G207-2 is illustrated in FIG. 4, which reveals that G207-1 and G207-2 are ten times more sensitive to ganciclovir than R3616. The ganciclovir sensitivity of R3616 is similar to wild-type. Each data point represents the mean of triplicates. The plaque number in the absence of ganciclovir represents 100% plaques. The dotted line indicates the $ED_{50}$.

Temperature Sensitivity of Mutant Viral Vector

To provide an additional safety feature that further compromises viral replication in the presence of encephalitis and fever, the sensitivity of the mutant viral vectors to temperatures greater than the basal temperature of the host are ascertained. Table 2 demonstrates the decreased plaquing efficiency of G207-1 and G207-2 at elevated temperatures. The plaque efficiencies were determined by titering virus stocks on Vero cell monolayers. Infected Vero cell monolayers are cultured with 1% IFCS medium at 37° C. or 39.5° C. and fixed at 48 hr postinfection. Plaques are counted following Giemsa staining. Titers are expressed as pfu/ml.

The hrR3 mutant showed temperature sensitivity compared to the parental strain KOS as previously reported. Goldstein and Weller, *Virology* 166: 41 (1988). The HSV-1 wild-type strain F, which is the parental strain of R3616, G207-1, and G207-2, is also temperature sensitive. The R3616, G207-1, and G207-2 mutants remain as temperature sensitive as their parental strains.

TABLE 2

Plaquing Efficiencies of KOS, hrR3, R3616, G207-1, and G207-2 on Vero Cells at 37° C. and 39.5° C.

| Virus | 37° C. | 39.5° C. |
|---|---|---|
| KOS | $1.6 \times 10^7$ | $6.6 \times 10^6$ |
| hrR3 | $3.6 \times 10^8$ | $<10^4$ |
| R3616 | $1.2 \times 10^9$ | $<10^5$ |
| G207-1 | $6.0 \times 10^7$ | $<10^4$ |
| G207-2 | $6.0 \times 10^7$ | $<10^4$ |

EXAMPLE 3

IN VIVO EXTRACRANIAL MODELS

Subcutaneous Glioma Xenograft Transplantation and Therapy

The effects of mutant herpes simplex virus infection on human brain tumors in vivo were assessed in athymic mice to allow for growth of the human tumors. Subcutaneous xenograft implantation was performed as previously described. Martuza et al., *Science* 252: 854 (1991) and Markert et. al., *Neurosurg.* 32: 597 (1993). To test the effect of the herpes simplex virus mutants on human glioma in vivo, 1 mm$^3$ minced glioma pieces (obtained from nude mice previously injected subcutaneously with cultured U-87MG cells) are implanted subcutaneously into nude mice. Nude mice are anesthetized with 0.25 ml of a solution consisting of 84% bacteriostatic saline, 10% sodium pentobarbitol (1 mg/ml), and 6% ethyl alcohol. Animals dying within 48 hours of any procedure are considered perioperative deaths and are excluded from analysis. Deaths in the subcutaneous tumor experiments are excluded from analysis (no significant difference in deaths occurred between virus-treated groups and their corresponding controls).

Between weeks 4 and 5, animals growing tumors (≧8 mm in diameter) are divided into two groups of 7 to 10 animals per group. Controls received intraneoplastic injections of 50 or 60 µl of DMEM+; treated animals received similar intraneoplastic injections of virus suspended in DMEM+. Doses administered for each virus vary between $10^6$ and $10^8$ plaque forming units. Care is taken to distribute virus throughout the tumor. For two-dose experiments, subsequent injections of DMEM+ or virus are made on Day 14. Similar experiments are conducted for each of the virus mutants at various doses.

Tumors were measured weekly or twice weekly with Vernier calipers. Growth of subcutaneous xenografts was recorded as the tumor growth ratio by formula $([l \times w \times h]/2)/([l \times w \times h]_{day0}/2)$ as described in Martuza et al., supra (1991). Growth ratio comparisons were made at 28 days after the initial treatment. Potential differences in growth ratios were assessed by use of the one-sided Wilcoxon rank test.

Subcutaneous Glioma Xenograft Therapy Using G207

Mice harboring subcutaneous tumors (approximately 6 mm in diameter) were randomly divided (n=6 per group) and treated intraneoplastically with either $5 \times 10^7$ pfu of G207 virus suspended in 0.05 ml virus buffer or with buffer alone. The tumor diameter was measured by external caliper measurements. For pathological studies, tumor-bearing mice (>10 mm in diameter) were treated with $1 \times 10^7$ pfu of G207 and sacrificed on day 8, 15 postinjection. Tumors were removed, placed in fixative for 1 hr and submerged in cold phosphate buffered saline. Tumors were then placed overnight in X-gal solution.

Figure 5:
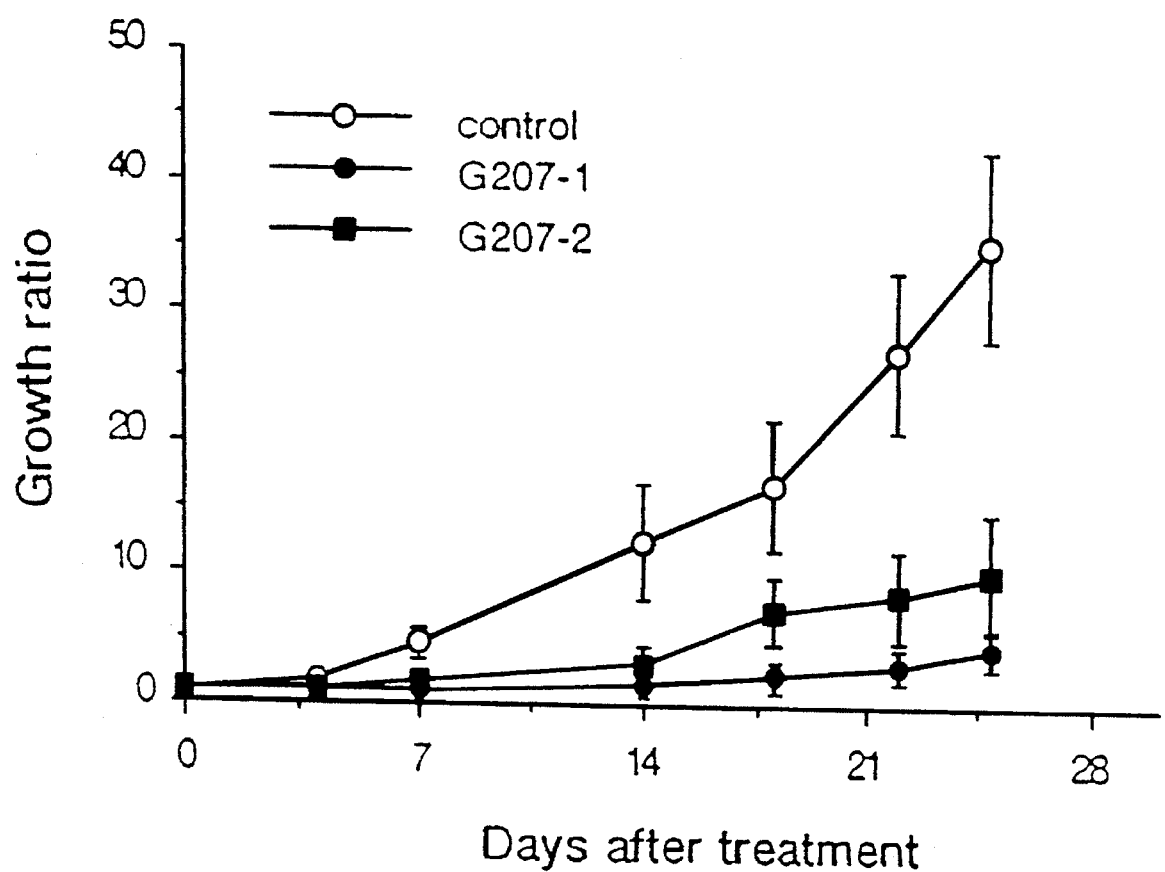
FIG. 5 is a graph illustrating the ability of G207-1 and G207-2 to inhibit the growth of human brain tumor cells (U-87MG) in the subcutaneous human brain tumor model in athymic mice.

FIG. 5 is a graph showing the growth ratio of subcutaneous U-87MG tumors in Balb/c (nu/nu) mice treated with $5 \times 10^7$ pfu of G207-1 (closed circle) or G207-2 (closed square) on Day 0, or with control medium alone (open circle). Tumors were measured twice weekly with calipers and the growth ratio calculated by dividing the tumor volume by the tumor volume on the day of initial inoculation. Bars represent mean ±SE for each group. The mean tumor growth rate was significantly inhibited in tumors treated with G207 compared to control tumors treated with medium alone.

Subrenal Capsule Model

The effects of G207 on U-87MG cells grown in the subrenal capsule of the nude mouse also would be tested because the subrenal capsule is a site used for monitoring growth of other nervous system tumors. Lee et al., *Neurosurg.* 26: 598 (1990); Medhkour et al., *J. Neurosurg.* 71: 545 (1989). U-87MG cells ($1.5 \times 10^6$) would be implanted in the subrenal capsule of nude mice. Ten days later, the tumors are measured and inoculated with varying pfus of G207 in 1 µl DME+ or 1 µl DME+ alone. All mice were re-examined at 14 days and 26 days following inoculation to measure tumor size. Virus-treated tumors that are smaller than control tumors show that the mutant virus is capable of killing tumor cells in vivo.

EXAMPLE 4

IN VIVO INTRACRANIAL TUMOR KILLING

To evaluate the in vivo efficacy of the replication-competent herpes simplex virus vector in treating intracerebral gliomas, nude mice would be stereotactically inoculated in the right frontal lobe with $1.6 \times 10^5$ U-87MG cells. In a pilot study, a similar cell inoculum caused 100% mortality within 1.5 months.

Ten days after tumor implantation, animals would be divided randomly into treatment groups to receive the following therapies at the same stereotactic coordinates used for the tumor implants: (1) the control group would receive intracranial inoculations of 6 µl DME+ as above, (2) the second group would receive intracranial inoculations of $10^3$ pfu (low-dose) of the mutant replication-competent viral vector, (3) the third group would receive intracranial inoculations of $10^5$ pfu (middle-dose) of the test virus, and (4) the fourth group would receive intracranial inoculations of $10^7$ pfu (high dose of the test virus), each suspended in 6 µl DME+. Inoculations would be in 2 µl DME+ at the stereotactic co-ordinates initially used to inject the U-87MG cells. By 7 weeks, all control animals would be dead, as they have been in past evaluations. A mutant viral vector of the instant invention is one that kills intracerebral brain tumors by keeping a significant number of the mice alive by seven weeks post-treatment. Significance is determined by plotting experimentals vs. controls in a one-tailed Fischer exact test.

In Vivo Neuropathology

The animals that remain healthy and neurologically normal at 19 weeks are sacrificed. The entire brain will be fixed, serially sectioned at 7 μm intervals, stained with hematoxylin and eosin, and microscopically examined for evidence of encephalitis and/or tumor. The absence of evidence of encephalitis would reveal that the viral vector possesses the characteristic of decreased or attenuated generalized neurovirulence. The absence of evidence of tumor would reveal that the viral vector is efficacious in killing human brain tumor cells in vivo.

In vivo treatment would be more effective for those herpes simplex virus mutants that exhibit decreased neurovirulence yet retain cytopathic effects in glioma cells because such vectors would allow tumor treatment at higher viral doses.

Studies of Herpes Simplex Virus Mutants in Immune Competent Animal Models

To test the efficacy of the herpes simplex virus mutants in killing human tumor cells in the presence of a competent immune system, the GL261 mouse ependymoblastoma model would be utilized in its syngeneic host, the C57BL/6 mouse. The GL261 cell line would be implanted subcutaneously or intracranially in C57BL/6 mice. Animals harboring subcutaneous GL261 tumors would be randomly divided and treated intraneoplastically as described above in the nude mouse model. The virus-treated group showing significant growth inhibition, as assessed by the Wilcoxon rank sum test would then be assayed in the intracranial studies.

For intracranial studies, mice would be injected with $10^4$ GL261 cells in the right frontal lobe. After 7 days, the animals would be inoculated intraneoplastically with either mutant virus or with medium alone. All of the media treated mice would probably die, as they have in previous studies. The viral mutants that would be capable of prolonging mouse survival to 40 days or longer after tumor cell implantation would be considered efficacious in killing human brain tumor cells in vivo.

Neuropathology and Tumor Killing in Herpes Simplex Virus-Immunized Animals

Since herpes simplex virus is endemic in society, an effective therapy would have to accommodate patients that have been exposed to HSV-1. Accordingly, it is important to determine whether the mutant herpes simplex virus vectors of the present invention can destroy tumor cells in situ in animals that have been previously immunized to herpes simplex virus. The effect of herpes simplex virus-immunization on the ability of the mutant viral vector to kill tumor cells in vivo would be tested in the GL261 intracranial model in C57BL/6 mice.

C57BL/6 mice would be immunized against the KOS strain of herpes simplex virus; another group of mice would be immunized with the wild-type strain from which the vector is derived; another group would be mock-immunized with saline. Those mice that demonstrate high serum titers of antibody by plaque reduction assay 2 weeks after inoculation would be used as herpes simplex virus-immunized animals. Four weeks after immunization, tumor cells would be injected intracerebrally as described above. One week later, the tumor would be inoculated at the same stereotactic coordinates with the vector using medium alone in the negative control group. The effect of pre-immunization on tumor cell growth, subsequent animal death, and the ability of herpes simplex virus to kill the tumor cells would be assessed as described for the intracerebral model.

In addition, several animals from each group would be sacrificed for a neuropathological study during each of the acute phase (2 days), subacute phase (1 week), and chronic phase (1 month and 3 months). The following histologic pathologies would be assessed: tumor size, immune cell infiltration, brain edema, necrosis, alteration of neurons, glia, myelination, hemorrhage, blood vessel proliferation or destruction, reactive astrocytes, normal neurons and glia, ischaemia, gliosis and the spread of virus (PCR for viral DNA or β-galactosidase). These studies would determine whether pre-immunization against herpes simplex virus has any effect on the mutant viral vector's ability to kill tumor cells or elicit neuropathogenesis.

Identification of Virus Location

Herpes simplex virus containing the E. coli LacZ gene and expressing β-galactosidase after viral infection is a useful marker for histologically determining the dynamics and spread of the tagged virus. Because the hrR3 mutant contains the E. coli LacZ gene inserted into the ICP6 gene such that the virus expresses β-galactosidase during viral replication, infected cells can be stained with X-gal. Goldstein and Weller, supra (1988).

This marker permits following the spread of virus in vivo by examining brain specimens from mice at various time points after infection with hrR3 by staining with X-gal. Kaplitt et al., Mol. & Cell. Neurosci. 2: 320 (1991). The presence of virally-infected cells in fixed brain sections is determined by PCR and compared to the proportion of X-gal staining cells. The tumor is visible after counter-staining with H&E or immunohistochemically with tumor-cell or species-specific markers. In this way, replication-competent viral vectors would be tracked and assessed for their ability to spread to tumor cell deposits at a distance from the main tumor mass. Histologic studies would determine the maximum distance that the virus can spread to reach a distant tumor deposit.

Another sensitive technique for identifying the presence of herpes simplex virus or defective herpes simplex virus vector in brain sections would employ PCR. In order to localize viral DNA, DNA for PCR would be isolated from cells after fixation and histochemistry such that even single positive cells would generate a specific PCR signal. Using specific oligonucleotide primers, unique PCR products would be generated from the viral vector DNA present in these cells. Cover slips would be removed from slides and small pieces of tissue would be dissected out. The tissue would be incubated with proteinase K, Tween-20, oligonucleotides and PCR buffer at 65° C. for 90 min. and then increased to 95° C. to inactivate proteinase K. The treated samples would be diluted with dNTPs, PCR buffer and Taq DNA polymerase and thermocycled. The PCR products then would be size analyzed by agarose gel electrophoresis. In addition, available in situ PCR techniques could be utilized to localize viral DNA during the neuropathological studies. Embretson et al., Proc. Nat'l Acad. Sci. USA 90: 357 (1993).

Safety of Replication-Competent Herpes Simplex Virus Mutants in Mice and Non-human Primates To establish that the herpes simplex virus vector does not produce neurovirulence at the dose required to kill tumor cells, animals receive inoculations of tumor-killing doses of the mutant herpes simplex virus vector to determine whether the vector would cause herpes simplex virus encephalitis in vivo. Aliquots (10 µl) of G-207-1, G-207-2 and strain F were inoculated into the right cerebral hemisphere of three week old mice; deaths were scored up to 21 days postinfection. Table 3 shows that the intracerebral inoculation of Balb/c mice with the parent wild-type virus (strain F) at $10^3$ p.f.u. caused half the animals to die from encephalitis. Chou et al., *Science* 250: 1262 (1990). The known $LD_{50}$ for strain 17 is also $10^3$ p.f.u.'s. McKie et ai., *J. Gen. Virol.*, 75: 733 (1994). In contrast, no mortality or illness was observed following intracerebral inoculation of the highest titers of G207-1 or G207-2 that we could produce ($10^7$ p.f.u. in 10 ul). The dose of $10^7$ p.f.u. was shown to kill tumor cells in vivo in the subcutaneous U-87MG tumor growth model, as shown in FIG. 5.

TABLE 3

Neurovirulence of G207-1 and G207-2 in Balb/c mice (i.c. injection for $LD_{50}$)

Balb/c mice (3 wks old) intracranial injection (10 µl)

| | | | |
|---|---|---|---|
| G207-1 | $1 \times 10^7$ pfu/10 µl | ×8 | (8/8, all mice alive) |
| G207-2 | $1 \times 10^7$ pfu/10 µl | ×8 | (8/8, all mice alive) |
| Strain F | $1 \times 10^3$ pfu/10 µl | ×8 | (4/8, 2 on day 3, 1 on day 5, 1 on day 14) |

*Aotus trivigatus*, a primate species exceedingly sensitive to herpes simplex virus encephalitis, is used to test the safety of the mutant herpes simplex virus vectors of the invention. Katzin et al, *Proc. Soc. Exp Biol. Med.* 125: 391 (1967); Melendez et al., *Lab. Anim. Care* 19: 38 (1969).

Magnetic Resonance Imaging (MRI) scanning or other imaging analysis would be used to assess encephalitis. Monkeys would receive a brain MRI with and without gadolinium prior to the start of the trial.

Initial testing would be performed at the highest dose that can be generated for the particular mutant that has been determined to be safe in mice ($LD_{10}$ or less). For example, $10^7$ pfu would be administered intracerebrally for the G207 deletion mutant to be tested. The dose that is well tolerated by a species known to be highly sensitive to herpes simplex virus, provides the most compelling evidence that this treatment would be reasonably safe in humans. If no clinical or MRI evidence of encephalitis is noted within 1 month, another animal would be tested at that same dose or at a log higher. The animal would be observed daily for signs of neurological and systemic illness.

This method can determine the maximal dose that can safely be administered intracranially without producing death, persistent neurological signs, or progressive illness. After 12 months, the animals would be sacrificed and the brains examined for loss or alteration of neurons, glial reaction, myelination, hemorrhage, blood vessel proliferation or destruction, viral DNA (by PCR) or virally-induced β-galactosidase in blood vessels, ischaemia, necrosis, gliosis, and inflammatory reaction. These studies would elucidate the neuropathologic lesions (if any) that might be expected to occur in the normal primate brain as a result of infection with this vector.

The genus Aotus had been long thought to be a monotypic genus with *Aotus trivigatus* as its sole representative. Studies have proved, however, that Aotus is a multispecific genus with species and subspecies ranging in chromosome number from 2n=46 to 2n=56 (*Aotus nancymai*, karyotype 1 owl monkey, 2n=54). When the susceptibility of owl monkeys to herpes simplex virus was reported in the 1960's, they could not distinguish *Aotus trivigatus* from *Aotus nancymai*. Malaga et al., *Lab. Anim. Sci.* 41: 143-45 (1991). Under current taxonomic classification, however, *Aotus nancymai* was formerly believed to represent *Aotus trivigatus*. Hershkovitz, *Amer. J. Primatol.* 4: 209 (1983).

Replication-competent viral vectors of the instant invention would be tested for their ability to produce herpes simplex virus encephalitis in primates that are sensitive to herpes simplex virus induced encephalitis, namely, *Aotus nancymai* and/or *Aotus trivigatus*. An *Aotus nancymai* is still living three weeks after being inoculated with $10^7$ pfu of the G207 mutant.

EXAMPLE 5

TREATMENT OF HUMAN BRAIN TUMORS WITH REPLICATION-COMPETENT VIRAL VECTORS

Patients with recurrent glioblastoma that was refractory to standard surgery, radiotherapy and chemotherapy would be treated with herpes simplex virus therapy. The patient would be scanned using MRI or CT or other technique and the tumor and normal brain registered in stereotactic space. The virus would be administered using stereotactically guided neurosurgical techniques. A computer tomography (CT) scan or magnetic resonance imaging (MRI) scan computes the stereotactic frame that would be used to accurately inoculate virus into a tumor at one or more locations. Virus would be inoculated at a dose of $10^1$ to $10^7$ p.f.u. per inoculation using a <2 mm cannula. The number of sites inoculated would depend on the size of the tumor. Patients would be followed with periodic MRI scans and with neurological examination, blood count, and liver function tests.

In an alternate scheme, patients will be operated to remove much of the recurrent tumor and virus will inoculated in the resected tumor bed in a fashion similar to above.

EXAMPLE 6

REPLICATION-COMPETENT HERPES SIMPLEX VIRUS VECTOR VACCINES

The herpes simplex virus vector of the invention can be used as a vaccine to protect an animal against herpes simplex virus infection. In the present context, "protecting" a subject against herpes simplex virus includes both (1) a prophylactic vaccine, i.e., a vaccine used to prevent a future herpes simplex virus infection, and (2) a therapeutic vaccine for treating an existing herpes simplex viral infection.

The herpes simplex virus sample would be prepared using standard methodology. Herpes simplex virus-infected Vero cells would be frozen at −70° C. until they are to be used. The material would be thawed and the cell debris would be pelleted by centrifugation. The supernatant fluid would be discarded and the pellet resuspended to its original volume. This material would most closely approximate that used in vaccine manufacture. This suspension would be sonicated twice for 20 seconds.

Herpes simplex virus plaque titers would be determined by standard procedures. For example, the virus would be titrated in triplicate on monolayers of Vero cells in 6-well plates. After adsorption of samples for 2 hours, cells would be overlayed with media containing 0.6% agarose and incubated at 37° C. in a CO$_2$-rich environment for 48 h. A second overlay, the same as above except for addition of neutral red, would be added and the cells would be incubated an additional 24 hours.

The herpes simplex virus pools would be titrated before filtration. The pools then would be filtered through a Nalgene 0.45 μm filter, sampled, refiltered through a second filter and then resampled.

EXAMPLE 7

TESTING OF HERPES SIMPLEX VIRUS-VACCINE FOR PATHOGENICITY IN A MURINE MODEL AND MONKEY MODEL

The lethality of the herpes simplex virus vaccine would be compared with the lethality of other herpes simplex virus vaccines in <24 h old suckling mice, CD-1 strain, (Charles River, Raleigh, N.C.). Meignier et al., *J. Infect. Diseases* 158: 602 (1988); Burke, *Curr. Topics in Microbiology and Immunology* 179: 137 (1992). Comparative titration of herpes simplex virus vector vaccine and wild type vaccines would be conducted in a single test using the final bulk of the herpes simplex virus vaccine.

Logarithmic dilutions of the vaccine would be prepared. Two litters of 5 mice each would be used for each dilution. Mice would be inoculated intracerebrally with 0.03 ml of the appropriate dilutions and observed for 21 days. Mouse lethality would be calculated as the dose in pfu that killed 50% of mice (e.g., pfu/0.03 ml of vaccine divided by $LD_{50}$ of vaccine).

Also, the herpes simplex virus vector would be given to 4 monkeys in the study. An additional six monkeys would receive the vector one year after immunization with the herpes simplex virus vector of the invention. If intradermal and subcutaneous administration of the vaccine candidate is well tolerated, the herpes simplex virus vector vaccine is deemed to be safe for use as an immunoprotective agent against herpes simplex virus.

In addition, all monkeys would be tested for serum antibody titers specific for herpes simplex virus. Monkey seroconversion would be measured by ELISA, after primary immunization. If all monkeys seroconvert, the herpes simplex virus vector vaccine is deemed to have efficacy as an immunoprotective agent against herpes simplex virus.

EXAMPLE 8

HUMAN CLINICAL STUDIES WITH HERPES SIMPLEX VIRUS VECTOR VACCINE

For use as a vaccine, the mutated herpes simplex virus vector of the invention would be inoculated subcutaneously. Thereafter, herpes simplex virus-specific antibody titers and herpes simplex virus-specific cell mediated response levels would be determined. Meignier et al., *J. Infect. Diseases* 162: 313 (1990); Burke, Curr. *Topics in Microbiology and Immunology* 179: 137 (1992). The preliminary phase of the study would involve an inoculation of four individuals with documented HSV-1 infections (Group 1), succeeded by inoculation of four HSV-1 -naive individuals (Group 2) 21 days after the first group had been inoculated. Previous HSV-1 exposure would be documented by medical records or unequivocal HSV-1 outbreak, as assessed by HSV-1 immunofluorescence assay available in clinical laboratories. This would be followed by a randomized trial in 24 herpes simplex virus-naive volunteers (Group 3). Anti HSV-1 immune globulin and anti-herpetic agents are available on site for the treatment of serious adverse reactions.

Group 1, 2, 3 and 4 subjects would be admitted to the hospital three days prior to inoculation and would remain as inpatients until four days after inoculation. Subjects would then be discharged and assessed on an outpatient basis with clinical examinations for potential reactions or complications through day 21. Subjects developing fever, rash, lethargy, necrotic skin lesions, or neurologic signs are followed with subsequent daily clinical examinations and admitted to the hospital if deemed necessary.

Group 5 volunteers, all HSV-1-naive, would be enrolled depending on availability as outpatient subjects. Group 5 volunteers would be randomly assigned to one of two subgroups: one would receive a single injection and the other would receive a booster.

Protocol participation studies would include periodic examinations of the following: CBC with differential and platelets, urinalysis, serum chemistries, serum viremia, serum herpes simplex virus antibody, and lymphocyte immune responses to herpes simplex virus antigen. Remaining serum samples would be maintained frozen at −80° to −120° C. and available for additional studies and/or repeats of selected studies as needed. Fluid in vesicular or weeping lesions at the site of inoculation or at distant sites would be sampled and placed in viral isolation transport medium to attempt virus recovery. Serum antibody determinations would include ELISA reactivity with cells infected with the herpes simplex virus vector, HSV-1 antigen and plaque reduction neutralization of HSV-1 viral vector.

Clinical trials of the herpes simplex virus vector should show the vaccine to be safe and effective in humans. Vaccine recipients would be expected to produce significant humoral response as measured by ELISA. A positive response would be characterized by the production of both neutralizing and non-neutralizing antibodies, the latter being measured by plaque reduction and neutralization assays. In addition, positive lymphocyte blastogenesis assays would be expected to demonstrate that lymphocytes from vaccine recipients proliferate and produce cytokines upon exposure to herpes simplex virus antigen in vitro.

What is claimed is:

1. A replication-competent herpes simplex virus that is incapable of expressing both (i) a functional $_{\gamma}34.5$ gene product and (ii) a ribonucleotide reductase.

2. A herpes simplex virus vector, wherein the genome of said vital vector contains alterations in both (i) the $_{\gamma}34.5$ gene and (ii) the ribonucleotide reductase gene, wherein said alterations prevent the expression of said genes or render the expressed products of said genes nonfunctional when a cell is transfected with said vector.

3. A method of preparing the replication-competent herpes simplex virus vector of claim 2, said method comprising the steps of:

(A) isolating a viral genome of a herpes simplex virus;

(B) permanently altering said genome so that neither a functional 34.5 gene product nor a functional ribonucleotide reductase is expressed when a cell is transfected with said vector and the virus (1) is sensitive to antiviral agents, (2) kills tumor cells, and (3) expresses decreased generalized neurovirulence.

4. The method of claim 3, wherein said herpes simplex virus is HSV-1.

5. The method of claim 3, wherein said herpes simplex virus is HSV-2.

6. A method of preparing the replication-competent herpes simplex virus of claim 1, said method comprising the steps of:

(A) isolating a viral genome of a herpes simplex virus;

(B) permanently altering said genome so that neither a functional 34.5 gene product nor a functional ribonucleotide reductase is expressed when a cell is infected with said virus and the virus (1) is sensitive to antiviral agents, (2) kills tumor cells, and 3) expresses decreased generalized neurovirulence; and (C) reconstituting a replication-competent herpes simplex virus having said permanently altered genome.

7. The method of claim 6, wherein said herpes simplex virus is HSV-1.

8. The method of claim 6, wherein said herpes simplex virus is HSV-2.

* * * * *